(12) United States Patent
Vaughn

(10) Patent No.: US 9,283,211 B1
(45) Date of Patent: *Mar. 15, 2016

(54) ORAL RAPAMYCIN PREPARATION AND USE FOR STOMATITIS

(71) Applicant: Rapamycin Holdings, Inc., San Antonio, TX (US)

(72) Inventor: Dana M Vaughn, Seguin, TX (US)

(73) Assignee: Rapamycin Holdings, LLC, San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/717,844

(22) Filed: May 20, 2015

Related U.S. Application Data

(63) Continuation of application No. PCT/US2015/026266, filed on Apr. 16, 2015.

(51) Int. Cl.
*A61K 31/436* (2006.01)
*A61K 9/00* (2006.01)

(52) U.S. Cl.
CPC ............. *A61K 31/436* (2013.01); *A61K 9/0053* (2013.01)

(58) Field of Classification Search
CPC .................................................. A61K 31/436
See application file for complete search history.

(56) References Cited

U.S. PATENT DOCUMENTS

| | | |
|---|---|---|
| 716,067 A | 12/1902 | Lemon et al. |
| 3,929,992 A | 12/1975 | Sehgal et al. |
| 3,993,749 A | 11/1976 | Sehgal et al. |
| 4,316,885 A | 2/1982 | Rakhit |
| 4,401,653 A | 8/1983 | Eng |

(Continued)

FOREIGN PATENT DOCUMENTS

| | | |
|---|---|---|
| CA | 2572100 A1 | 6/2007 |
| CA | 2734828 A1 | 2/2010 |

(Continued)

OTHER PUBLICATIONS

Ai-Ling, L et al, "Chronic Rapamycin Restores Brain Vascular Integrity and Function Through NO Synthase Activation and Improves memory in Symptomatic Mice Modeling Alzheimer's Disease", Journal of Cerebral Blood Flow & Metabolism, vol. 33, 1412-1421, Sep. 2013.

(Continued)

*Primary Examiner* — Benjamin Packard
(74) *Attorney, Agent, or Firm* — William H. Quirk; Jesse L. Frizzell; Rosenthal Pauerstein Sandoloski Agather LLP

(57) ABSTRACT

The disclosure teaches counter-intuitive methods for treating stomatitis using oral mTOR inhibiting preparations such as preparations of microcapsules and nanoparticles including an inhibitor of the mammalian target of rapamycin. The methods, preparations and other teachings are useful in various respects, especially for assisting in the treatment, prevention and management of stomatitis in feline subjects and, most especially, the treatment and management of Feline Chronic Gingivo-Stomatitis (FCGS), with secondary applications also related to management of gingivitis and autoimmune mucosal disorders. Disclosed embodiments illustrate multi-week dosing regimens and also address needs for alternative preparations or manufacturing processes that ensure efficacy while improving other performance characteristics such as storage stability, biodistribution, dosage cost, etc.

21 Claims, 8 Drawing Sheets

(56) References Cited

U.S. PATENT DOCUMENTS

| | | |
|---|---|---|
| 4,460,722 A | 7/1984 | Igarashi et al. |
| 4,885,171 A | 12/1989 | Surendra et al. |
| 5,023,262 A | 6/1991 | Caufield et al. |
| 5,023,263 A | 6/1991 | Burg |
| 5,023,264 A | 6/1991 | Caufield et al. |
| 5,066,493 A | 11/1991 | Sehgal et al. |
| 5,078,999 A | 1/1992 | Warner et al. |
| 5,080,899 A | 1/1992 | Sturm et al. |
| 5,100,883 A | 3/1992 | Schiehser |
| 5,100,899 A | 3/1992 | Calne |
| 5,102,876 A | 4/1992 | Caufield |
| 5,118,677 A | 6/1992 | Caufield |
| 5,118,678 A | 6/1992 | Kao et al. |
| 5,120,725 A | 6/1992 | Kao et al. |
| 5,120,726 A | 6/1992 | Failli et al. |
| 5,120,727 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,151,413 A | 9/1992 | Caufield et al. |
| 5,162,333 A | 11/1992 | Failli et al. |
| 5,164,399 A | 11/1992 | Failli et al. |
| 5,169,851 A | 12/1992 | Hughes et al. |
| 5,177,203 A | 1/1993 | Failli et al. |
| 5,194,447 A | 3/1993 | Kao |
| 5,202,332 A | 4/1993 | Hughes et al. |
| 5,206,018 A | 4/1993 | Sehgal et al. |
| 5,221,670 A | 6/1993 | Caufield |
| 5,221,740 A | 6/1993 | Hughes |
| 5,233,036 A | 8/1993 | Hughes |
| 5,260,299 A | 11/1993 | Failli et al. |
| 5,260,300 A | 11/1993 | Hu |
| 5,262,423 A | 11/1993 | Kao |
| 5,262,424 A | 11/1993 | Kao |
| 5,286,731 A | 2/1994 | Caufield et al. |
| 5,288,711 A | 2/1994 | Mitchell et al. |
| 5,302,584 A | 4/1994 | Kao et al. |
| 5,310,903 A | 5/1994 | Goulet et al. |
| 5,321,009 A | 6/1994 | Baeder et al. |
| 5,344,833 A | 9/1994 | Hughes |
| 5,346,893 A | 9/1994 | Failli et al. |
| 5,358,944 A | 10/1994 | Caufield |
| 5,362,718 A | 11/1994 | Skotnicki et al. |
| 5,373,014 A | 12/1994 | Failli et al. |
| 5,378,696 A | 1/1995 | Caufield |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,411,967 A | 5/1995 | Kao et al. |
| 5,434,260 A | 7/1995 | Skotnicki et al. |
| 5,446,048 A | 8/1995 | Failli et al. |
| 5,463,048 A | 10/1995 | Skotnicki et al. |
| 5,480,988 A | 1/1996 | Failli et al. |
| 5,480,989 A | 1/1996 | Kao et al. |
| 5,484,790 A | 1/1996 | Failli et al. |
| 5,484,791 A | 1/1996 | Failli et al. |
| 5,486,522 A | 1/1996 | Failli et al. |
| 5,486,523 A | 1/1996 | Failli et al. |
| 5,486,524 A | 1/1996 | Failli et al. |
| 5,488,054 A | 1/1996 | Failli et al. |
| 5,489,595 A | 2/1996 | Failli et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,504,204 A | 4/1996 | Failli et al. |
| 5,504,291 A | 4/1996 | Goble et al. |
| 5,508,285 A | 4/1996 | Nelson et al. |
| 5,508,286 A | 4/1996 | Skotnicki et al. |
| 5,508,290 A | 4/1996 | Nelson et al. |
| 5,508,399 A | 4/1996 | Kao et al. |
| 5,516,780 A | 5/1996 | Skotnicki et al. |
| 5,519,031 A | 5/1996 | Skotnicki et al. |
| 5,521,194 A | 5/1996 | Nelson et al. |
| 5,525,610 A | 6/1996 | Caufield et al. |
| 5,530,007 A | 6/1996 | Kao et al. |
| 5,530,121 A | 6/1996 | Kao et al. |
| 5,532,355 A | 7/1996 | Skotnicki et al. |
| 5,536,729 A | 7/1996 | Waranis et al. |
| 5,541,191 A | 7/1996 | Skotnicki et al. |
| 5,541,192 A | 7/1996 | Skotnicki et al. |
| 5,550,133 A | 8/1996 | Failli et al. |
| 5,552,160 A | 9/1996 | Liversidge et al. |
| 5,559,112 A | 9/1996 | Skotnicki et al. |
| 5,559,119 A | 9/1996 | Skotnicki et al. |
| 5,559,120 A | 9/1996 | Kao et al. |
| 5,559,121 A | 9/1996 | Harrison et al. |
| 5,559,122 A | 9/1996 | Nelson et al. |
| 5,561,138 A | 10/1996 | Armstrong |
| 5,563,145 A | 10/1996 | Failli et al. |
| 5,567,709 A | 10/1996 | Skotnicki et al. |
| 5,637,590 A | 6/1997 | Skotnicki et al. |
| 5,665,772 A | 9/1997 | Cottens et al. |
| 5,780,462 A | 7/1998 | Lee et al. |
| 5,891,469 A | 4/1999 | Amselem |
| 5,912,253 A | 6/1999 | Cottens et al. |
| 5,922,730 A | 7/1999 | Hu et al. |
| 5,932,243 A | 8/1999 | Fricker et al. |
| 5,952,373 A | 9/1999 | Lanzendorfer et al. |
| 5,955,457 A | 9/1999 | Lee et al. |
| 5,985,890 A | 11/1999 | Cottens et al. |
| 5,989,591 A | 11/1999 | Nagi |
| 6,004,973 A | 12/1999 | Guitard et al. |
| 6,015,809 A | 1/2000 | Zhu et al. |
| 6,197,781 B1 | 3/2001 | Guitard et al. |
| 6,200,985 B1 | 3/2001 | Cottens et al. |
| 6,204,243 B1 | 3/2001 | Posanski |
| 6,228,396 B1 | 5/2001 | Watts |
| RE37,421 E | 10/2001 | Holt et al. |
| 6,329,386 B1 | 12/2001 | Mollison |
| 6,386,869 B1 | 5/2002 | Zegarelli |
| 6,399,625 B1 | 6/2002 | Zhu |
| 6,440,990 B1 | 8/2002 | Cottens et al. |
| 6,475,518 B1 | 11/2002 | Baumgart et al. |
| 6,486,099 B2 | 11/2002 | Igari et al. |
| 6,503,883 B1 | 1/2003 | Posanski |
| 6,537,195 B2 | 3/2003 | Forman |
| 6,555,132 B1 | 4/2003 | Brox et al. |
| 6,569,463 B2 | 5/2003 | Patel et al. |
| 6,592,916 B2 | 7/2003 | Soeda et al. |
| 6,596,268 B1 | 7/2003 | Coffey et al. |
| 6,605,298 B1 | 8/2003 | Leigh et al. |
| 6,649,157 B2 | 11/2003 | Coffey et al. |
| 6,653,256 B1 | 11/2003 | Wolf |
| 6,670,355 B2 | 12/2003 | Azrolan et al. |
| 6,677,357 B2 | 1/2004 | Zhu et al. |
| 6,680,330 B2 | 1/2004 | Zhu et al. |
| 6,923,988 B2 | 8/2005 | Patel et al. |
| 6,929,818 B2 | 8/2005 | Luthra et al. |
| 6,936,644 B2 | 8/2005 | Gilleo |
| 6,956,043 B2 | 10/2005 | Guitard et al. |
| 6,974,473 B2 | 12/2005 | Barclay et al. |
| 7,008,979 B2 | 3/2006 | Schottman et al. |
| 7,037,582 B2 | 5/2006 | Xing et al. |
| 7,041,046 B2 | 5/2006 | Forman |
| 7,041,283 B1 | 5/2006 | Achim et al. |
| 7,084,171 B2 | 8/2006 | Grainger et al. |
| 7,132,458 B2 | 11/2006 | Burton et al. |
| 7,160,867 B2 | 1/2007 | Abel et al. |
| 7,220,755 B2 | 5/2007 | Betts et al. |
| 7,241,771 B2 | 7/2007 | Zhu |
| 7,268,144 B2 | 9/2007 | Gu et al. |
| 7,271,177 B2 | 9/2007 | Benjamin et al. |
| 7,273,874 B2 | 9/2007 | Graziani et al. |
| 7,276,498 B2 | 10/2007 | Graziani et al. |
| 7,279,562 B2 | 10/2007 | Molnar-Kimber et al. |
| 7,282,505 B2 | 10/2007 | Zhu et al. |
| 7,292,885 B2 | 11/2007 | Scott et al. |
| 7,304,033 B2 | 12/2007 | Larsen et al. |
| 7,345,053 B2 | 3/2008 | Garvey |
| 7,445,916 B2 | 11/2008 | Gu et al. |
| 7,446,111 B2 | 11/2008 | Benjamin et al. |

(56) References Cited

U.S. PATENT DOCUMENTS

| | | |
|---|---|---|
| 7,452,723 B2 | 11/2008 | Coffey et al. |
| 7,455,853 B2 | 11/2008 | Mollison et al. |
| 7,470,682 B2 | 12/2008 | Graziani et al. |
| 7,476,678 B2 | 1/2009 | Graziani et al. |
| 7,488,444 B2 | 2/2009 | Furst et al. |
| 7,517,342 B2 | 4/2009 | Scott et al. |
| 7,517,362 B2 | 4/2009 | Shanley et al. |
| 7,519,418 B2 | 4/2009 | Scott et al. |
| 7,538,119 B2 | 5/2009 | Gu et al. |
| 7,541,380 B2 | 6/2009 | Bianchi et al. |
| 7,560,457 B2 | 7/2009 | Graziani et al. |
| 7,576,903 B2 | 8/2009 | Yamamoto et al. |
| 8,007,831 B2 | 8/2011 | Lewis et al. |
| 8,053,444 B2 | 11/2011 | Reven et al. |
| 8,343,926 B2 | 1/2013 | Nagy |
| 2001/0026807 A1 | 10/2001 | Watts |
| 2002/0009473 A1 | 1/2002 | Tebbe |
| 2003/0106382 A1 | 6/2003 | Shukla et al. |
| 2003/0176455 A1 | 9/2003 | Adelman |
| 2003/0215496 A1 | 11/2003 | Patel et al. |
| 2004/0010002 A1 | 1/2004 | Wasik et al. |
| 2004/0074089 A1 | 4/2004 | Gilleo |
| 2004/0121155 A1 | 6/2004 | Matsunami et al. |
| 2005/0090553 A1 | 4/2005 | Shapiro |
| 2005/0113282 A1 | 5/2005 | Parekh et al. |
| 2006/0115533 A1 | 6/2006 | Guitard et al. |
| 2006/0121122 A1 | 6/2006 | Nakajima et al. |
| 2006/0210638 A1 | 9/2006 | Liversidge et al. |
| 2006/0234053 A1 | 10/2006 | Yamamoto et al. |
| 2006/0251710 A1 | 11/2006 | Kwon et al. |
| 2006/0251720 A1 | 11/2006 | Penhasi et al. |
| 2006/0264453 A1 | 11/2006 | Mudumba et al. |
| 2007/0082829 A1 | 4/2007 | Smets et al. |
| 2007/0138673 A1 | 6/2007 | Lee et al. |
| 2007/0142423 A1 | 6/2007 | Graziani et al. |
| 2007/0185150 A1 | 8/2007 | Bedrosian |
| 2007/0203168 A1 | 8/2007 | Zhao |
| 2007/0203169 A1 | 8/2007 | Zhao |
| 2007/0203170 A1 | 8/2007 | Zhao |
| 2007/0203171 A1 | 8/2007 | Zhao |
| 2007/0203172 A1 | 8/2007 | Zhao |
| 2007/0225313 A1 | 9/2007 | Zhao |
| 2007/0280992 A1 | 12/2007 | Margaron et al. |
| 2008/0022965 A1 | 1/2008 | Bysveen et al. |
| 2008/0069797 A1 | 3/2008 | Roncarolo et al. |
| 2008/0085880 A1 | 4/2008 | Viswanath et al. |
| 2008/0091008 A1 | 4/2008 | Viswanath et al. |
| 2008/0138405 A1 | 6/2008 | Raheja et al. |
| 2008/0182867 A9 | 7/2008 | Wasik et al. |
| 2008/0188511 A1 | 8/2008 | Beckmann et al. |
| 2008/0193653 A1 | 8/2008 | Oh |
| 2008/0214595 A1 | 9/2008 | Izumo et al. |
| 2008/0234380 A1 | 9/2008 | Shapiro |
| 2008/0249123 A1 | 10/2008 | Gu et al. |
| 2008/0275076 A1 | 11/2008 | Holm et al. |
| 2010/0105637 A1 | 4/2010 | Kim |
| 2010/0105696 A1 | 4/2010 | Garcia-Echeverria et al. |
| 2010/0150864 A1 | 6/2010 | Hickman et al. |
| 2010/0303901 A1 | 12/2010 | Shimoni et al. |
| 2011/0104256 A1 | 5/2011 | Wang et al. |
| 2011/0105387 A1 | 5/2011 | Wu et al. |
| 2011/0195966 A1 | 8/2011 | Garcia-Echeverria et al. |
| 2011/0200556 A1 | 8/2011 | Gutkind et al. |
| 2011/0293731 A1 | 12/2011 | Lewis et al. |
| 2011/0311596 A1 | 12/2011 | Ngo et al. |
| 2012/0064143 A1 | 3/2012 | Sharp et al. |
| 2012/0122913 A1 | 5/2012 | Charbonneau et al. |
| 2012/0276169 A1 | 11/2012 | Kang et al. |
| 2015/0202164 A1* | 7/2015 | Vail et al. ............ 424/470 |

FOREIGN PATENT DOCUMENTS

| | | |
|---|---|---|
| CA | 2743491 A1 | 5/2010 |
| CN | 102292078 A | 12/2011 |
| EP | 778023 A | 6/1997 |
| EP | 1393747 A1 | 3/2004 |
| EP | 1709974 A2 | 10/2006 |
| EP | 2320894 A1 | 5/2011 |
| EP | 2322163 A1 | 5/2011 |
| EP | 2365802 A2 | 9/2011 |
| WO | 9531194 A1 | 11/1995 |
| WO | 2001097809 A2 | 12/2001 |
| WO | 2005034916 A1 | 4/2005 |
| WO | 2007093346 A1 | 8/2007 |
| WO | 2008022256 A2 | 2/2008 |
| WO | 2009133141 A2 | 11/2009 |
| WO | 2009133142 A1 | 11/2009 |
| WO | 2010022243 A1 | 2/2010 |
| WO | 2010056754 A2 | 5/2010 |
| WO | 2011009193 A1 | 1/2011 |
| WO | 2014059295 A1 | 4/2014 |
| WO | 2014144346 A1 | 9/2014 |
| WO | 2014144405 A1 | 9/2014 |

OTHER PUBLICATIONS

Bell, R and Zlokovic, B, "Neurovascular mechanisms and Blood-Brain Barrier Disorder in Alzheimer's Disease", Acta Neuropathology, Jul. 2009, 118(1): 103-113.

Caccamo, A et al, "Molecular Interplay Between Mammalian Target of Rapamycin (mTOR), Amyloid-β, and Tau", Journal of Biological Chemistry, Apr. 23, 2010, vol. 285, No. 17, p. 13107-13121.

Halloran, J et al, "Chronic Inhibition of mTOR by Rapamycin Modulates Cognitive and Non-Cognitive Components of Behavior Throughout Lifespan in Mice", Neuroscience, Jun. 2012, vol. 223: p. 102-113, US.

Jhunjhunwala, J et al, Delivery of Rapamycin to Dendritic Cells Using Degradable Microparticles, US National Library of medicine, National Institutes of Health, Feb. 10, 2009; 133(3) 191-197 doi: 10.1016/j.conrel,2008.10.011.

Majumder, S et al, "Inducing Autophagy by Rapamycin Before, but Not After, the Formation of Plaques and Tangles Ameliorates Cognitive Deficits", PLos One, Sep. 2011, vol. 6, Issue 9, Emory University, US.

Parlar, A et al, "Posttransplantation Therapeutic Rapamycin Concentration Protects Nitric Oxide-Related Vascular Endothelial Function: Comparative Effects in Rat Thoracic Aorta and Coronary Endothelial Cell Culture", Jun. 2010, Transplantation Proceedings, Elsevier Inc., Orlando, FL, vol. 42(5), p. 1923-1930.

Ravikumar, B et al, "Rapamycin Pre-Treatment Protects Against Apoptosis", Human Molecular Genetics, vol. 15, No. 7,p. 1209-1216, Apr. 2006, Oxford University Press, Surrey, United Kingdom.

Spilman, P et al, "Inhibition of MTOR by Rapamycin Abolishes Cognitive Deficits and Reduces Amyloid-β Levels in a Mouse Model of Alzheimer's Disease", Apr. 2010, vol. 5, Issue 4, PLoS One vol. 5(4): p. e9979.

Zlokovic, B, "Neurovascular Pathways to Neurodegeneration in Alzheimer's Disease and Other Disorders", National Rev Neuroscience, vol. 12(12): p. 723-738.

Blagosklonny, "An anti-aging drug today: from senescence-promoting genes to anti-aging pill," Drug Discov Today. Mar. 2007;12(5-6):218-24.

Carter et al., "Molecular mechanisms of life- and health-span extension: role of calorierestriction and exercise intervention," Appl Physiol Nutr Metab. Oct. 2007;32(5):954-66.

Guertin and Sabatini, "The pharmacology of mTOR inhibition," Sci. Signal., 2(67):pe24, 2009.

Petroulakis et al., "mTOR signaling: implications for cancer and anticancer therapy," Br. J.Cancer, 96(Suppl.):R11-R15, 2007.

Pickford et al., "The autophagy-related protein beclin 1 shows reduced expression in earlyAlzheimer disease and regulates amyloid beta accumulation in mice ," J. Clin. Invest.,118:2190-2199, 2008.

Powers III et al., "Extension of chronological life span in yeast by decreased TOR pathwaysignaling," Genes & Development, 20:174-184, 2006.

Ravikumar et al., "Aggregate-prone proteins with polyglutamine and polyalanine expansionsare degraded by autophagy," Hum Mol Genet. May 1, 2002;11(9):1107-17.

(56) References Cited

OTHER PUBLICATIONS

Rosner and Hengstschläger, "Cytoplasmic and nuclear distribution of the protein complexesmTORC1 and mTORC2: rapamycin triggers dephosphorylation and delocalization of themTORC2 components rictor and sin1," Hum Mol Genet. Oct. 1, 2008;17(19):2934-48.
Saganich et al., "Deficits in synaptic transmission and learning in amyloid precursor protein(APP) transgenic mice require C-terminal cleavage of APP," J. Neurosci., 26:13428-13436,2006.
Sarkar et al., "Rapamycin and mTOR-independent autophagy inducers ameliorate toxicity ofpolyglutamine-expanded huntingtin and related proteinopathies," Cell Death Differ. Jan. 2009;16(1):46-56.
Schwecke et al., "The biosynthetic gene cluster for the polyketide immunosuppressantrapamycin ," Proc. Natl. Acad. Sci. USA, 92(17):7839-7843, 1995.
Sharp and Bartke, "Evidence for down-regulation of phosphoinositide 3-kinase/Akt/mammaliantarget of rapamycin (PI3K/Akt/mTOR)-dependent translation regulatory signaling pathways inAmes dwarf mice ," J. Gerontol. A Biol. Sci. Med. Sci., 60:293-300, 2005.
Shima et al., "Disruption of the p70(s6k)/p85(s6k) gene reveals a small mouse phenotype and anew functional S6 kinase ," Embo J., 17:6649-6659, 1998.
Skeen et al., "Akt deficiency impairs normal cell proliferation and suppresses oncogenesis in ap53-independent and mTORC1-dependent manner ," Cancer Cell, 10:269-280, 2006.
Steffen et al., "Yeast life span extension by depletion of 60s ribosomal subunits is mediated byGcn4," Cell. Apr. 18, 2008;133(2):292-302.
Steinhilb et al., "Tau phosphorylation sites work in concert to promote neurotoxicity in vivo," Mol Biol Cell. Dec. 2007;18(12):5060-8.
Steinkraus et al., "Dietary restriction suppresses proteotoxicity and enhances longevity by anhsf-1-dependent mechanism in Caenorhabditis elegans," Aging Cell. Jun. 2008;7(3):394-404.
Suzuki et al., "The pre-autophagosomal structure organized by concerted functions of APGgenes is essential for autophagosome formation," EMBO J., 20:5971-5981, 2001.
Tremblay et al., "Overactivation of S6 kinase 1 as a cause of human insulin resistance duringincreased amino acid availability," Diabetes, 54:2674-2684, 2005.
Tsang et al., "Targeting mammalian target of rapamycin (mTOR) for health and diseases," Drug Discovery Today, 12 (3/4):112-124, 2007.
Tsuchiya et al., "Sirtuin-independent effects of nicotinamide on lifespan extension from calorierestriction in yeast," Aging Cell. Dec. 2006;5(6):505-14.
Um et al., "Nutrient overload, insulin resistance, and ribosomal protein S6 kinase 1, S6K1,"Cell Metab., 3:393-402, 2006.
Wei et al., "Life span extension by calorie restriction depends on Rim15 and transcriptionfactors downstream of Ras/PKA, Tor, and Sch9," PLoS Genet. Jan. 2008;4(1):e13.
Wei et al., "Tor1/Sch9-regulated carbon source substitution is as effective as calorie restrictionin life span extension," PLoS Genet. May 2009;5(5):e1000467.
Xie et al., "Insights into TOR function and rapamycin response: chemical genomic profiling byusing a high-density cell array method," Proc Natl Acad Sci U S A. May 17, 2005;102(20):7215-20. Epub May 9, 2005. Erratum in: Proc Natl Acad Sci U S A. Sep. 5, 2006;103(36):13560. Proc Natl Acad Sci U S A. Jun. 13, 2006;103(24):9374.
Yeh et al., "Rapamycin inhibits clonal expansion and adipogenic differentiation of 3T3-L1cells," Proc. Natl. Acad. Sci. USA, 92:11086-11090, 1995.
Yu et al., "Macroautophagy—a novel Beta-amyloid peptide-generating pathway activated inAlzheimer's disease," J Cell Biol. Oct. 10, 2005;171(1):87-98.
Zhang et al., "Small molecule regulators of autophagy identified by an image-based highthroughputscreen," Proc Natl Acad Sci U S A. Nov. 27, 2007;104(48):19023-8.
"Sirolimus," Wikipedia website located at http://en.wikipedia.org/wiki/Rapamycin, downloaded Oct. 20, 2009.
Aguilar et al., "S6 kinase deletion suppresses muscle growth adaptations to nutrient availabilityby activating AMP kinase," Cell Metab, 5:476-487, 2007.
An et al., "Mechanism of zinc-induced phosphorylation of p70 S6 kinase and glycogensynthase kinase 3beta in SH-SY5Y neuroblastoma cells," J Neurochem. Mar. 2005;92(5):1104-15.
An et al., "Up-regulation of phosphorylated/activated p70 S6 kinase and its relationship toneurofibrillary pathology in Alzheimer's disease," Am J Pathol. Aug. 2003;163(2):591-607.Erratum in: Am J Pathol. Dec. 2003;163(6):2645.
Balan et al., "Life span extension and neuronal cell protection by Drosophila nicotinamidase," JBiol Chem. Oct. 10, 2008;283(41):27810-9.
Banko et al., "The translation repressor 4E-BP2 is critical for eIF4F complex formation,synaptic plasticity, and memory in the hippocampus," J. Neurosci., 25:9581-9590, 2005.
Billings et al., "Intraneuronal Abeta causes the onset of early Alzheimer's disease-relatedcognitive deficits in transgenic mice," Neuron, 45:675-688, 2005.
Bisht et al., "In vivo characterization of a polymeric nanoparticle platform with potential oraldrug delivery capabilities," Mol Cancer Ther. Dec. 2008;7(12):3878-88.
Blagosklonny, "Aging and immortality: quasi-programmed senescence and its pharmacologicinhibition," Cell Cycle. Sep. 2006;5(18):2087-102.
Blagosklonny, "Paradoxes of aging," Cell Cycle. Dec. 15, 2007;6(24):2997-3003.
Boland et al., "Autophagy induction and autophagosome clearance in neurons: relationship toautophagic pathology in Alzheimer's disease," J Neurosci. Jul. 2, 2008;28(27):6926-37.
Caccamo et al., "Rapamycin rescues TDP-43 mislocalization and the associated low molecularmass neurofilament instability," J Biol Chem. Oct. 2, 2009;284(40):27416-24.
Cao et al., "Toll-like receptor-mediated induction of type I interferon in plasmacytoid dendriticcells requires the rapamycin-sensitive PI(3)K-mTOR-p70S6K pathway," Nat Immunol. Oct. 2008;9(10):1157-64.
Chen et al., "HIF-1 modulates dietary restriction-mediated lifespan extension via IRE-1 in Caenorhabditis elegans," PLoS Genet. May 2009;5(5):e1000486.
Choo et al., "Rapamycin differentially inhibits S6Ks and 4E-BP1 to mediate cell-type-specificrepression of mRNA translation," Proc. Natl. Acad. Sci. USA, 105(45):17414-9, 2008.
d'Abramo et al., "Troglitazone, a peroxisome proliferator-activated receptor-gamma agonist,decreases tau phosphorylation in CHOtau4R cells," J Neurochem. Aug. 2006;98(4):1068-77.
Damjanac et al., "PKR, a cognitive decline biomarker, can regulate translation via twoconsecutive molecular targets p53 and Redd1 in lymphocytes of AD patients," J Cell Mol Med. Aug. 2009;13(8B):1823-32.
Dhahbi et al., "Temporal linkage between the phenotypic and genomic responses to caloricrestriction," Proc. Natl Acad. Sci. USA, 101:5524-5529, 2004.
Edwards et al., "Annual report to the nation on the status of cancer, 1973-1999, featuringimplications of age and aging on U.S. cancer burden," Cancer, 94:2766-2792, 2002.
Estep et al., "Short-term calorie restriction in male mice feminizes gene expression and alterskey regulators of conserved aging regulatory pathways," PLoS One. 2009;4(4):e5242.
Fajadet et al., "Randomized, double-blind, multicenter study of the Endeavor zotarolimuselutingphosphorylcholine-encapsulated stent for treatment of native coronary artery lesions:clinical and angiographic results of the ENDEAVOR II trial," Circulation. Aug. 22, 2006;114(8):798-806.
Galvan et al., "Long-term prevention of Alzheimer's disease-like behavioral deficits in PDAPPmice carrying a mutation in Asp664," Behav. Brain Res., 191:246-255, 2008.
Galvan et al., "Reversal of Alzheimer's-like pathology and behavior in human APP transgenicmice by mutation of Asp664," Proc. Natl. Acad. Sci. USA, 103:7130-7135, 2006.
Gingras et al., "Hierarchical phosphorylation of the translation inhibitor 4E-BP1," Genes Dev.,15:2852-2864, 2001.
Guertin and Sabatini, "Defining the role of mTOR in cancer," Cancer Cell, 12:9-22, 2007.
Hansen et al., "A role for autophagy in the extension of lifespan by dietary restriction in C. elegans," PLoS Genetics, 4(2):e24, 2008.

* cited by examiner

ORAL RAPAMYCIN PREPARATION AND USE FOR STOMATITIS

CROSS-REFERENCE TO RELATED APPLICATION

The subject matter of this application relates to the subject matter of U.S. patent application Ser. No. 13/128,800, filed Nov. 11, 2009, published under Publication No. 2012/0064143, entitled "Inhibition of Mammalian Target of Rapamycin," which has original priority dating to Nov. 11, 2008 (for reference, the "Related UT Application"). Subject matter disclosed or claimed in this patent application has been developed in cooperation with representatives of the Board of Regents of the University of Texas System and Southwest Research Institute, which are assignees of record for the Related UT Application.

CLAIM OF PRIORITY TO PRIOR APPLICATION(S)

The present application claims the priority benefit of prior filed International Patent Application Number PCT/US15/26266, entitled "Oral Rapamycin Preparations and Use for Stomatitis," filed in the U.S. Receiving Office on Apr. 16, 2015, which claims priority to prior filed U.S. Provisional Patent Application Ser. No. 61/980,095, entitled "Oral Rapamycin Nanoparticle Preparations and Use in the Treatment of Inflammatory Gum Disease in Cats", filed on Apr. 16, 2014. By this reference, the full disclosures, including the claims and drawings, of International Patent Application Number PCT/US15/26266 and U.S. Provisional Application, Ser. No. 61/980,095, are incorporated herein as though now set forth in their entireties.

STATEMENT REGARDING FEDERALLY SPONSORED RESEARCH

Not directly applicable for this patent application, although the United States government may have certain rights in the subject matter of the Related UT Application.

BACKGROUND

1. Field of the Invention

The present invention relates generally to feline healthcare and particularly to prevention, treatment and management of stomatitis, most particularly feline chronic gingivo-stomatitis (FCGS). More particularly, aspects of the invention relate to manufacture and use of orally administered pharmaceutical preparations for prevention, treatment and management of feline chronic gingivo-stomatitis (FCGS).

2. Description of Related Art

For these purposes, "stomatitis" refers generically to any oropharyngeal inflammation and related processes of the mucous membranes in or around the mouth and oropharyngeal tissues of a subject. When stomatitis involves inflammation of the gums (i.e., gingiva), it can be generally referred to as gingivo-stomatitis, irrespective of whether mucous membranes other than the gums are also inflamed. To make more specific reference to inflammation of the gums, however, it is sometimes referred to as just "gingivitis." Because of the critical association between the gums and dental hygiene, for which numerous consumer products are targeted, at least for human healthcare markets, most consumers are somewhat familiar with the "gingivitis" term, although any form of gingivo-stomatitis can lead to serious complications.

Although the risks and challenges of gingivo-stomatitis can be serious for any species, gingivo-stomatitis can be especially devastating in feline populations. The "chronic" aspect of FCGS applies if a cat's natural healing mechanisms are unable to reverse the condition, which is often presumed if a cat's gingivo-stomatitis does not resolve within thirty days of onset or initial diagnosis. Once the condition progresses to a chronic condition, then, unfortunately, the prognosis for cats with FCGS tends to be life changing. Many veterinarians routinely consider full mouth dental extraction and root removal as the most practical treatment for, possibly even an essential part of, managing FCGS.

Though domestic cats can often live long lives despite dental extraction, the resulting lifestyle limitations can be life altering. A cat's teeth are not only important for eating, but also for self-defense. Moreover, their teeth often play an important role in their social relationships, especially with male cats, as a male cat will typically use its teeth to hold onto the neck of a female cat during copulation. Other challenges can be understood from published scientific literature on the subject, such as the December 2010 article entitled "*The Disease Formerly Known as Lymphocytic/Plasmacytic Gingivo-Stomatitis*," which can be accessed on the Internet through the website located at URL www.toothvet.ca, which is incorporated herein in its entirety by this reference.

Despite the well-known and long-felt needs for developing a pharmaceutical intervention for FCGS, no pharmaceutical interventions have demonstrated sufficient efficacy to be recognized as a routine intervention option for veterinarians. Moreover, even if one were contemplating active ingredients for preventing, treating or managing FCGS without the benefit of the present invention and impermissible hindsight, the teachings of the present invention would not be realistic candidates. Not only are Applicant's present teachings not known to be efficacious in the art of treating FCGS, but such teachings would likely be summarily dismissed from consideration even if a related thought ever arose. Such summarial dismissal would seem inevitable, largely because, if for no other reason, many have assumed that some aspects of the present invention present a material risk of ulcerating oropharyngeal tissues.

Irrespective of the state of art in the present field, for some applications far outside the scope and field of the present invention, rapamycin (also known as sirolimus) is a well-known pharmaceutical agent. Most notably, rapamycin has long been successfully used to minimize organ transplant rejection in humans, while seemingly countless other potential applications have also been postulated from time to time.

Rapamycin and its numerous analogs and derivatives (collectively known as "rapalogs") famously act to inhibit its namesake metabolic pathway in mammals—the mammalian target of rapamycin ("mTOR"). The critical metabolic roles of the mTOR pathway have long led to broad speculation about possible medical uses for rapamycin and rapalogs, in addition to rapamycin's well-known efficacy in reducing human organ transplant rejection. However, despite the success with prevention of transplant rejection, and despite the many long-felt needs and corresponding tremendous efforts in developing rapamycins for other indications, effective use of rapamycin or other rapalogs for treating or preventing other disorders has not been widely successful and has been very limited at best. The reader should refer to the Related UT Application, which has been incorporated by reference, for additional technical descriptions and a detailed description that relates to fields other than organ transplant.

Particular formulations taught in the Related UT Application (the "2008 Discoveries") provided particles or "cores"

containing the active rapamycin ingredient, and those cores were microencapsulated within a protective polymer matrix, for oral administration of the rapamycin. The rapamycin cores were preferably microencapsulated using a spinning disk atomization coating process with a protective polymer matrix known under the "EUDRAGIT® S 100" name. The EUDRAGIT® S 100 polymer matrix principally consists of a particular methacrylate polymer that is generally stable at pH levels below 7 and was thought to protect rapamycin from degrading in acidic conditions of the stomach. Then, once the microencapsulated rapamycin entered neutral or basic conditions (i.e., pH greater than or equal to 7) within the intestines, the protective matrix would be able to dissolve and, theoretically, un-degraded rapamycin would then be bioavailable for absorption through the intestinal walls of the subject. However, despite tremendous hope for broad efficacy of orally administered use of such microencapsulated rapamycin preparations, and despite widespread national and international attention to the 2008 Discoveries, commercial acceptance of the 2008 Discoveries has been minimal if not non-existent, as formidable challenges have remained.

Still, though, referring again to the field of the present invention, there remain long-felt unresolved needs in improving feline healthcare by providing an efficacious pharmaceutical preparation for treating and otherwise managing FCGS. Many other secondary needs and objectives will be understood by those of skill in the art.

SUMMARY OF THE INVENTION

While the present invention is multifaceted and can be embodied in many other forms, some aspects of the invention are embodied as methods or preparations for treating feline chronic gingivo-stomatitis (FCGS) and related conditions. Some embodiments also relate to preventing or managing FCGS and related conditions. Some teachings are also embodied as methods of administering improved forms of microencapsulated rapamycins and in methods for reliably producing and administering such improved forms relative to subjects. Related embodiments also represent pharmaceutical preparations that would be suitable for such uses, as well as methods for making such pharmaceutical preparations. Even in the event embodiments are not well described in those terms, the reader of skill in feline healthcare arts should still understand the characteristics of these embodiments based on the modes of invention and the various embodiments that are described hereafter.

Even though the invention relates primarily to feline healthcare and to prevention, treatment and management of FCGS and related conditions, many of the methods and preparations of the present invention involve improved forms of microencapsulated rapamycins, most preferably in the form of nanoparticles containing mTOR inhibitors stabilized and protected within a methyl methacrylate polymer matrix. Characteristics of such preparations are particularly beneficial for improving the stability of the subject mTOR inhibitor and for improving its bioavailability despite oral administration. The resulting preparations are not only more durable and stable, but are also more bioavailable and efficacious for treatment, prevention and management of feline chronic gingivo-stomatitis (FCGS). Such preparations also improve stability and bioavailability of rapamycin or other mTOR inhibitors for use in preventing, treating or managing autoimmune mucosal disorders and their precursors, concomitants and sequelae in humans and other animal subjects.

In some disclosed methods of administering a preparation and some disclosed methods of treatment, mTOR inhibiting preparations are administered in any desired manner. However, preferred embodiments involve making or obtaining preparations of rapamycin or an analog of rapamycin that is orally administered to the subject in multiple dosings over a multi-week period.

The compositions administered to the subjects preferably comprise rapamycin, or an analog of rapamycin or an alternate mTOR inhibitor. The more preferred forms of such compositions include a nanoparticle construct combined with a carrier material, preferably an enteric composition, for purposes of minimizing degradation of the composition until it passes the pylorus to the intestines of the subject. Compositions comprising rapamycin or an analog of rapamycin may also include a hydrophilic, swellable, hydrogel-forming material. Such compositions may be encased in a coating that includes a water insoluble polymer and a hydrophilic water permeable agent. In some embodiments, the water insoluble polymer is a methyl methacrylate-methacrylic acid copolymer. Compositions comprising rapamycin or an analog of rapamycin may further include a thermoplastic polymer for purposes of gradual or controlled release of the rapamycin or an analog of rapamycin. Examples of the thermoplastic polymer include EUDRAGIT® Acrylic Drug Delivery Polymers (Evonik Industries AG, Germany).

In some preferred preparations that are used for preventing, treating or managing the targeted maladies, rapamycin particles or particles of rapamycin analogs or other mTOR inhibitors or analogs thereof, are encapsulated or coated. In other preferred preparations, a more complex composition that includes the rapamycin or other mTOR inhibitor or analog thereof is encapsulated or coated. For reference purposes in these descriptions, "microencapsulation" (and its grammatical variations) should be interpreted to refer to protection of microparticle or nanoparticle forms of rapamycins (preferably in the nanoparticle forms according to the descriptions herein) by combining such particles with an enteric coating material or the like that is formulated to resist degradation in acidic conditions while allowing for more ready dissolution when exposed to basic conditions. Some preferred embodiments include amphoteric aqueous-soluble compounds, which is or includes sodium cholate or its analogs in some preferred preparations.

In some embodiments of the invention, amphoteric aqueous-soluble compounds are used to induce the formation of micelles. With embodiments that involve micelles, the method for making the composition preferably causes dispersed rapamycin to be concentrated in a pharmaceutically-active core within the micelle, thereby creating mTOR inhibiting nanoparticles, although other forms of mTOR inhibiting nanoparticles are also included within the scope of broader aspects of the invention. Stability of the mTOR inhibitor and/or the mTOR inhibiting nanoparticles is preferably enhanced by a carrier material. The type of carrier materials may vary in alternative embodiments, while methyl methacrylate compounds or other enteric coating materials are preferred, such as for example the compounds marketed under the EUDRAGIT® designation, most preferably the EUDRAGIT® S 100 compound.

The designations "microencapsulated rapamycin" and "enteric-coated rapamycin" are used interchangeably to refer generically to each and every variation of microencapsulated rapamycins, especially to those variations that are described or particularly suggested in these descriptions, and equivalents thereof. Exceptions in particular contexts should be understood, nonetheless, to the extent that the context makes more specific or contrary clarifications for that context. In some embodiments, the encapsulant or coating used for and incorporated in enteric-coated rapamycin preparations may be an enteric coating. In another aspect of these descriptions, general references to "prevention and treatment" (or the like) of a malady should be interpreted to include reference not only to prevention and treatment of the actual malady, but also to delay or reduction in the progression of that malady as well as prevention and treatment of its precursors, concomitants and sequelae.

In many embodiments involving enteric-coated rapamycin preparations, the rapamycins or other mTOR inhibitors, or related compositions that include the enteric-coated rapamycin preparations, are provided in the form of nanoparticles that include the rapamycin or other mTOR inhibitor within a pharmaceutically active core. In such cases, the designation "nanoRapa" is generically used for reference purposes in these descriptions. While the form of rapamycins used for a described embodiment may preferably include (but not be limited to) an encapsulated form of a nanoRapa preparation, such encapsulated forms of nanoparticles are occasionally designated for purposes of this application as "enteric-coated rapamycin nanoparticles."

Preparation of many embodiments incorporates steps including formation of a solution of rapamycin or other mTOR inhibitor, formation of a surfactant solution, and a step of combining the mTOR inhibitor and the surfactant solutions. In some preferred preparations, use of a surfactant solution preferably includes use of sodium cholate or a surfactant that is capable of promoting micelle formation.

After preparing or otherwise obtaining nanoRapa preparations through any of various approaches that may be understood and/or described herein, the nanoRapa preparation may then be coated with an enteric coating to provide an enteric-coated rapamycin preparation formed from nanoRapa particles. For reference purposes in these descriptions, the designation "enteric-coated nanoRapa" is generically used to refer to each and every enteric-coated rapamycin variation formed from nanoRapa particles.

Many other objects, features and advantages of the present invention will become apparent to those of ordinary skill in the art, particularly after a thorough review of the public literature in the field, and all the more from the following detailed descriptions and accompanying illustrations and claims. It should be understood, however, that the detailed description and the specific examples, while indicating preferred embodiments of the invention, are given by way of illustration only, since various changes and modifications within the spirit and scope of the invention will become apparent to those skilled in the art from these detailed descriptions.

BRIEF DESCRIPTION OF THE DRAWINGS

The accompanying drawings form part of the present specification and are included to further demonstrate and illustrate certain aspects of the present invention. The invention may be better understood by reference to one or more of these drawings in combination with the detailed description of specific embodiments presented herein.

DETAILED DESCRIPTION OF PREFERRED EMBODIMENTS

Figure 1:
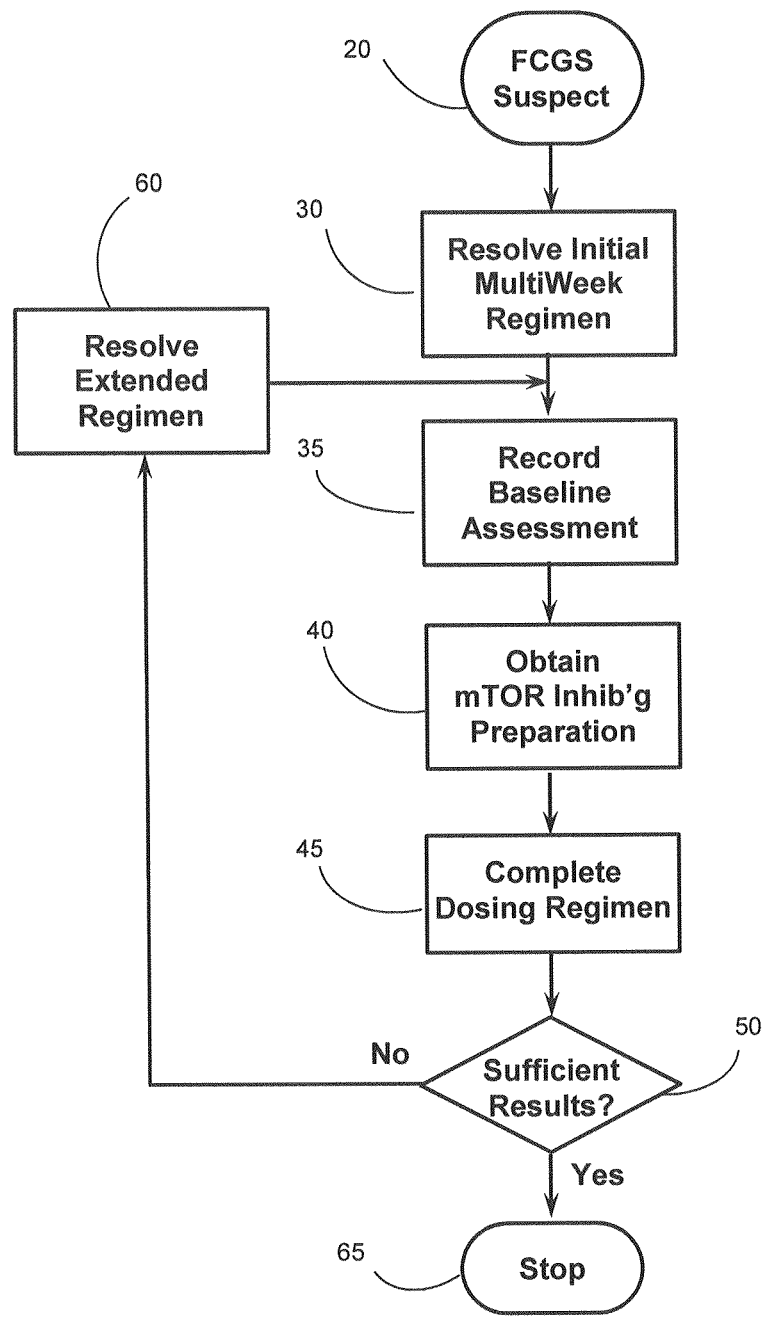
FIG. 1 is a flowchart illustration of a basic approach for preferred methods for using teachings of the present invention in response to a case of suspected FCGS, which also provides an illustrative reference for other methods and embodiments described in more detail in the text.

The following descriptions are provided to illustrate further detail of preferred embodiments of the invention. It should be appreciated by those of skill in the art that the treatment protocols, formulations and techniques disclosed are thought to represent embodiments that function well in the practice of the invention, and thus can be considered to constitute preferred modes for its practice. However, in light of the present disclosure, those of skill in the art should also appreciate that many changes can be made in any of these embodiments and the way they work while still obtaining equivalent results, without departing from the spirit and scope of the invention.

For purposes of these descriptions, a few wording simplifications should be understood as universal, except to the extent otherwise clarified in a particular context either in the specification or in any claims related to these descriptions. The use of the term "or" is used to mean "and/or" unless explicitly indicated to refer to alternatives only, or unless the alternatives are inherently mutually exclusive. When referencing values, the term "about" is used to indicate an approximate value, generally one that at least includes values within a standard deviation of error for any particular embodiments that are disclosed or for methods that are commonly used for determining such value. "A" or "an" may mean one or more, unless clearly indicated otherwise. Such "one or more" meanings are most especially intended when references are made in conjunction with open-ended words such as "having," "comprising" or "including." Likewise, "another" may mean at least a second or more.

Treating & Managing FCGS & Other Stomatitis Related Conditions

Basic aspects of the present invention enable pharmaceutical preparations and associated treatment regimens that are surprisingly successful in treating and otherwise managing stomatitis, most particularly for feline chronic gingivo-stomatitis (FCGS). Although numerous variations are contemplated for applying the invention in the treatment and management of FCGS and related health conditions, preferred embodiments involve a regimen of orally-administering stable preparations of mTOR inhibitors multiple times per week over a multi-week duration. While further particulars will be understood in the course of these descriptions, first are described various approaches for producing or otherwise obtaining suitable mTOR inhibitor preparations, many of which are suitable for use in practicing the methods of the present invention. Later portions of these descriptions also describe particular examples of how the invention has been and can be used in practice.

More particularly, multi-week regimens of orally administered microencapsulated mTOR-inhibiting nanoparticles are surprisingly effective in treating and reducing the severity of FCGS. Although potential dosing variations will also be understood to those of skill in the art, these descriptions will further elaborate on particular examples that are known to deliver preferred mTOR inhibitors in bioavailable amounts that have now been found to be clearly efficacious for reducing the severity of FCGS in most feline subjects. Indeed, some subjects that had quantifiable levels of FCGS upon commencement of a multi-dose treatment regimen appear to be fully cured of FCGS after just two weeks of following a preferred regimen, and it may well be that those subjects were fully cured even prior to completion of the two-week duration. These and other aspects of how to practice the invention will be described with reference to specific examples further in these descriptions.

Despite more rapid results in some subjects, the most reliable regimens of the present invention involve oral administration of stable mTOR-inhibiting preparations multiple times per week over durations of four weeks or more. Preferred regimens follow a daily administration of the mTOR inhibiting preparations, while other dosing regimens of every other day or three-times-per-week are also suitable. To achieve optimum pharmacokinetics, it should be readily understood by those of skill in the art that optimal daily doses generally contain smaller quantities of the bioavailable mTOR inhibitor than do less frequent doses.

Vice versa, it should also be understood that the amount of bioavailable mTOR inhibitor per dose can be reduced below preferred levels of a daily dose as needed, so long as other accommodations are made to ensure ingestion and metabolic absorption of efficacious amounts of the mTOR inhibitor. As one example of an alternative using smaller amounts of bioavailable mTOR inhibitor per dose, although daily oral administration is thought to be as frequent as would be necessary for achieving efficacious levels in a subject, smaller bioavailable amounts per dose of the mTOR inhibitor can be used as alternatives if for some reason a regimen is desired with multiple oral administrations per day. Those of skill in the art can readily determine suitable dose characteristics for such multiple administrations per day by resolving the equivalent of any of the daily doses described herein.

Based in part on the various studies described herein and the surprisingly efficacious results demonstrated by such studies, preferred methods of treating or managing FCGS have been developed. With reference to the flowchart of FIG. 1, there is shown a context for general characteristics of such preferred methods. Preferably, a preferred method is commenced once a veterinarian determines that a feline subject is suspected of having FCGS, as represented by Starting Point 20 in FIG. 1. In practice, Starting Point 20 preferably includes a visual assessment of the condition of the subject's oropharyngeal mucous membranes by a properly trained veterinarian or feline healthcare specialist. Though not illustrated in detail in FIG. 1, Starting Point 20 may also be embodied or practiced in a manner to include conducting more confirmatory tests or the like that reach the level of clearly establishing that the subject has FCGS. Starting Point 20 may also be embodied to include various steps to eliminate other solutions which may include adjusting nutrition, the presence of an underlying infection or other dental conditions (e.g., dental cleaning to remove plaque that can exacerbate gingival irritation) to the extent such steps can be easily completed without risk to the subject.

Though not separately shown in FIG. 1, preferred methods also include a preparatory regimen prior to administration of the first dose of the mTOR inhibitor. Preferred preparatory regimens include (a) one or more dental cleanings, (b) a period of antibiotic pre-treatment to ensure that the subject's stomatitis cannot be fully addressed without resort to an mTOR-inhibiting regimen, and (c) assessing, photographing and otherwise establishing a baseline for measuring progress during treatment with an mTOR-inhibiting regimen. One or more dental cleanings are preferably part of the preparatory regimen in order to minimize plaque and other secondary factors that may irritate the gums or otherwise contribute to or exacerbate FCGS. Further dental cleanings and tissue management measures may also be in order during the course of administering the mTOR inhibitor, according to physician discretion.

With respect to antibiotic pre-treatments, the general purpose for as much is to ensure that the subject's stomatitis cannot be fully addressed by treating an underlying infection, without resort to an mTOR-inhibiting regimen. The preferred duration for such a pre-treatment is two weeks, although other durations will be understood as alternatives for achieving much the same purposes. If the severity of the subjects' stomatitis is not significantly reduced after a reasonable period of antibiotic pre-treatment, then the FCGS is understood to be refractory, and if not resolved after 30 days of alternative treatment attempts, the FCGS is confirmed as chronic.

As illustrated next in the flowchart of FIG. 1, once observations made cause the veterinarian or other caregiver to at least suspect, or even know, that the subject has FCGS at Starting Point 20, the veterinarian or caregiver then resolves the desired characteristics for an initial multi-week regimen of administering mTOR inhibiting preparations to the subject, which is illustrated as Step 30 in the flowchart of FIG. 1. The initial multi-week regimen to be followed is preferably about two weeks or longer in duration, and it preferably involves administration of mTOR-inhibiting preparations in doses and at frequencies in accordance with other descriptions in this document. Preferably, the resolved regimen administers such preparations in a manner such that said feline subject ingests amounts of a pharmaceutically active mTOR inhibitor compound prepared according to the teachings in other portions of this description, in amounts and frequencies and over durations that are efficacious for reducing the severity of, and preferably to fully cure, FCGS in the feline subject.

After the initial regimen is resolved at Step 30, the initial multi-week dosing regimen is followed for the initial duration, as represented by Step 45 in FIG. 1. However, before commencing that dosing regimen 45, it is also preferred that the veterinarian staff create an initial baseline record of the subject's FCGS, as illustrated at Step 35. The Step 35 of recording an initial baseline assessment preferably includes charting the extent of the FCGS, compiling photographs or diagrams of affected tissue, and conducting an assessment of FCGS severity using recognized FCGS severity rating scales, such as the 4-point scale described elsewhere herein.

Particular regimens for administration of the mTOR inhibitor according to the present invention preferably involve oral administration of enteric-coated rapamycin nanoparticles in capsule form, over the duration of the multi-week initial regimen, which is preferably a four- or six- or eight-week duration. Recording the initial baseline assessment at Step 35 preferably serves to later aid in assessing progress, by providing a baseline for comparison to the results after administering the mTOR-inhibiting treatment regimen as herein described.

Though less critical, establishing an initial baseline at Step 35 may also include performing biopsies of affected tissue, such as were performed in the course of the studies described elsewhere herein. Such biopsies may be taken by punch biopsy or excision prior to enteric-coated rapamycin nanoparticles administration at an initial oral examination. For comparison and assessment of progress, such biopsies may again be taken following the oral examination at the termination of treatment regimen, which is preferably part of Decision Point 50 in FIG. 1. When an initial baseline assessment at Step 35 involves a biopsy, the site of the biopsy is preferably selected from a region of greatest inflammation that is large enough such that subsequent biopsies can also be performed in the same area for comparison. For best comparisons, a final biopsy will preferably be taken from a region of tissue immediately adjacent to the original biopsy site.

By comparing to the initial baseline record established at Step 35 after completion of the initial regimen at Step 45, the Decision Point 50, which asks whether the results of the initial regimen are sufficient, can be more readily and reliably completed. If the results are sufficient, then treatment may be stopped, as represented by Stopping Point 65 in FIG. 1; whereas if the results are considered insufficient by the veterinarian, she or he can then resolve the characteristics of a second multi-week regimen of administering mTOR-inhibiting preparations according to the teachings of the present invention, as represented by Step 60 in FIG. 1. The characteristics for an extended regimen resolved at Step 60 can be much the same as the initial regimen, although the dosing amount and/or frequency may be increased in the discretion of the veterinarian so long as maximum tolerable doses are not likely to be exceeded. The same repeating cycle can be repeated indefinitely until the veterinarian concludes that completion of any particular regimen has produced results sufficient to stop the treatments. Although negative results would understandably be very disappointing, it should be understood that a conclusion to stop the treatment at Decision Point 50 may involve results that sufficiently demonstrate that the FCGS will not likely respond to further multi-week administration regimens.

In addition to treatment of FCGS, alternative embodiments for some aspects of the invention are achieved by administering the same or analogous mTOR inhibitor regimens for prevention, treatment or management of conditions related to FCGS. For these purposes, conditions related to FCGS include not only FCGS but also any of the various forms of stomatitis and its precursors, concomitants and sequelae in feline subjects, as well as any of the various forms of stomatitis and its precursors, concomitants and sequelae in non-feline subjects. Still other embodiments are achieved by administering the same or analogous mTOR inhibitor regimens for prevention, treatment or management of related conditions such as any of the various forms of stomatitis and its precursors, concomitants and sequelae in non-feline animal subjects, which include human subjects in some alternatives. It will be understood, nonetheless, that variations in the dosing regimens described herein may be suitable and even beneficial depending on the species of animal of the subject, and also depending on the nature of the stomatitis-related condition for which the regimen is being applied.

Although preferred embodiments involve treatment of FCGS and related conditions, some aspects of the invention may be appreciated in the prevention, treatment and management of various other indications as well. Preferred embodiments of oral administration protocols according to the present invention are more stable, more bioavailable and efficacious, and find better biodistribution for treatment and prevention and reducing the progression of genetically-predisposed disorders and age-related disorders, with surprising benefits especially in the field of the prevention and treatment of gingivitis in felines and are thought to have analogous benefits in humans and other animals.

Pharmaceutical Preparations

Many of the methods of the present invention involve administration of MTOR inhibitors. Any inhibitor of mTOR is contemplated for inclusion in the present compositions and methods. In particular embodiments, the inhibitor of mTOR is rapamycin or an analog of rapamycin, preferably administered orally in the form of an enteric-coated rapamycin and/or enteric-coated nanoRapa preparation.

Rapamycin binds to a member of the FK binding protein (FKBP) family, FKBP 12. The rapamycin/FKBP 12 complex binds to the protein kinase mTOR to block the activity of signal transduction pathways. Because the mTOR signaling network includes multiple tumor suppressor genes, including PTEN, LKB1, TSC1, and TSC2, and multiple proto-oncogenes including P13K, Akt, and eEF4E, mTOR signaling plays a central role in cell survival and proliferation. Binding of the rapamycin/FKBP complex to mTOR causes arrest of the cell cycle in the G1 phase (Janus 2005).

Inhibitors of mTOR also include rapamycin analogs. Many rapamycin analogs are known in the art. Non-limiting examples of analogs of rapamycin include, but are not limited to, everolimus, tacrolimus, CC1-779, ABT-578, AP-23675, AP-23573, AP-23841, 7-epi-rapamycin, 7-thiomethyl-rapamycin, 7-epi-trimethoxyphenyl-rapamycin, 7-epi-thiomethyl-rapamycin, 7-demethoxy-rapamycin, 32-emethoxy-rapamycin, 2-desmethyl-rapamycin, and 42-O-(2-hydroxy) ethyl rapamycin.

For purposes of these descriptions, absent clear limitation otherwise, other analogs of rapamycin include: rapamycin oximes (U.S. Pat. No. 5,446,048); rapamycin aminoesters (U.S. Pat. No. 5,130,307); rapamycin dialdehydes (U.S. Pat. No. 6,680,330); rapamycin 29-enols (U.S. Pat. No. 6,677,357); O-alkylated rapamycin derivatives (U.S. Pat. No. 6,440,990); water soluble rapamycin esters (U.S. Pat. No. 5,955,457); alkylated rapamycin derivatives (U.S. Pat. No. 5,922,730); rapamycin amidino carbamates (U.S. Pat. No. 5,637,590); biotin esters of rapamycin (U.S. Pat. No. 5,504,091); carbamates of rapamycin (U.S. Pat. No. 5,567,709); rapamycin hydroxyesters (U.S. Pat. No. 5,362,718); rapamycin 42-sulfonates and 42-(N-carboalkoxy) sulfamates (U.S. Pat. No. 5,346,893); rapamycin oxepane isomers (U.S. Pat. No. 5,344,833); imidazolidyl rapamycin derivatives (U.S. Pat. No. 5,310,903); rapamycin alkoxyesters (U.S. Pat. No. 5,233,036); rapamycin pyrazoles (U.S. Pat. No. 5,164,399); acyl derivatives of rapamycin (U.S. Pat. No. 4,316,885); reduction products of rapamycin (U.S. Pat. Nos. 5,102,876 and 5,138,051); rapamycin amide esters (U.S. Pat. No. 5,118,677); rapamycin fluorinated esters (U.S. Pat. No. 5,100,883); rapamycin acetals (U.S. Pat. No. 5,151,413); oxorapamycins (U.S. Pat. No. 6,399,625); and rapamycin silyl ethers (U.S. Pat. No. 5,120,842).

For purposes of these descriptions, absent clear limitation otherwise, still other analogs of rapamycin include those described in U.S. Pat. Nos. 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; 5,023,262; all of which are incorporated herein by reference. Additional rapamycin analogs and derivatives can be found in the following U.S. Patent Application Pub. Nos., all of which are herein specifically incorporated by reference: 20080249123, 20080188511; 20080182867; 20080091008; 20080085880; 20080069797; 20070280992; 20070225313; 20070203172; 20070203171; 20070203170; 20070203169; 20070203168; 20070142423; 20060264453; and 20040010002.

Rapamycin or a rapamycin analog can be obtained from any source known to those of ordinary skill in the art. The source may be a commercial source or a natural source. Rapamycin or a rapamycin analog may be chemically synthesized using any technique known to those of ordinary skill in the art. Non-limiting examples of information concerning rapamycin synthesis can be found in Schwecke et al., 1995; Gregory et al., 2004; Gregory et al., 2006; and Graziani, 2009.

Preferred embodiments of the present invention provide an improved form of encapsulated rapamycin—an encapsulated rapamycin nanoparticle that is more durable, stable and bioavailable, which enhances efficacy and predictability and ensures better biodistribution while also allowing improved patient compliance relative to raw rapamycin, as well as being produced at a reasonable cost. The improved form of encapsulated rapamycin preferably provides the rapamycin nanoparticles within a polymer matrix, forming an encapsulated rapamycin nanoparticle in a single drug delivery structure for oral administration of rapamycin. The polymer matrix, more particularly, is a controlled-release matrix, as described elsewhere in these descriptions. This encapsulated rapamycin nanoparticle may also be referred to as an enteric-coated rapamycin nanoparticle. In addition, many of the preferred embodiments also include a stabilizing compound (for our purposes, a "stabilizer") within the controlled-release matrix either to improve compatibility of the rapamycin with the controlled-release matrix, to stabilize the crystalline morphology of the rapamycin, or to help further prevent degradation of the rapamycin, particularly when the encapsulated rapamycin nanoparticle is exposed to air, atmospheric moisture, or room temperature or warmer conditions. Particularly preferred embodiments incorporate the stabilizers within each rapamycin nanoparticle, although certain aspects of the invention may be embodied with stabilizers on the surface of the encapsulated rapamycin nanoparticles or otherwise dispersed in the controlled-release matrix. To different levels, depending on the particular approach used for producing the nanoparticles, with or without other additives, the result is more efficacious for treatment and prevention of diseases and/or disorders in humans and other animals.

Rapid anti-solvent precipitation, or controlled precipitation, is a preferred method of preparing the rapamycin nanoparticles as it provides for minimal manipulation of the rapamycin and exquisite control over nanoparticle size and distribution, and the crystallinity of the rapamycin. Several controlled precipitation methods are known in the art, including rapid solvent exchange and rapid expansion of supercritical solutions, both of which can be implemented in batch or continuous modes, are scalable, and suitable for handling pharmaceutical compounds. Preferred embodiments use an anionic approach, producing micelles 130 (illustrated in FIG. 2) or other molecular aggregations of amphipathic compounds (e.g. sodium cholate or similar surfactants with amphipathic tendencies) in concentrations greater than their critical micelle concentrations. Such amphipathic compounds also preferably exhibit amphoteric properties when utilized for micelle formation.

Figure 2:
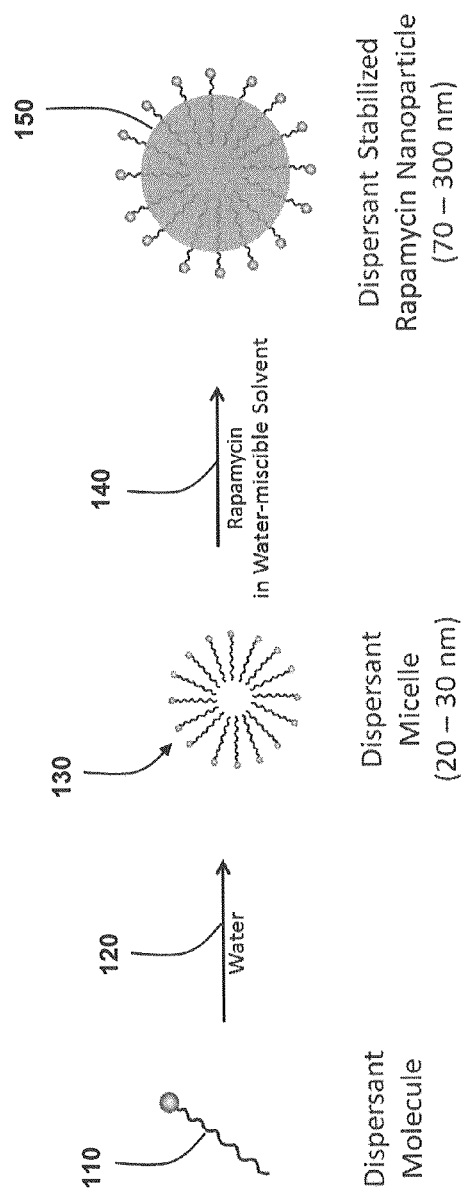
FIG. 2 is a graphic illustration of microscopic aspects of a preferred process for producing a dispersion of preferred forms of rapamycin nanoparticles according to the teachings of the present invention.
Figure 3:
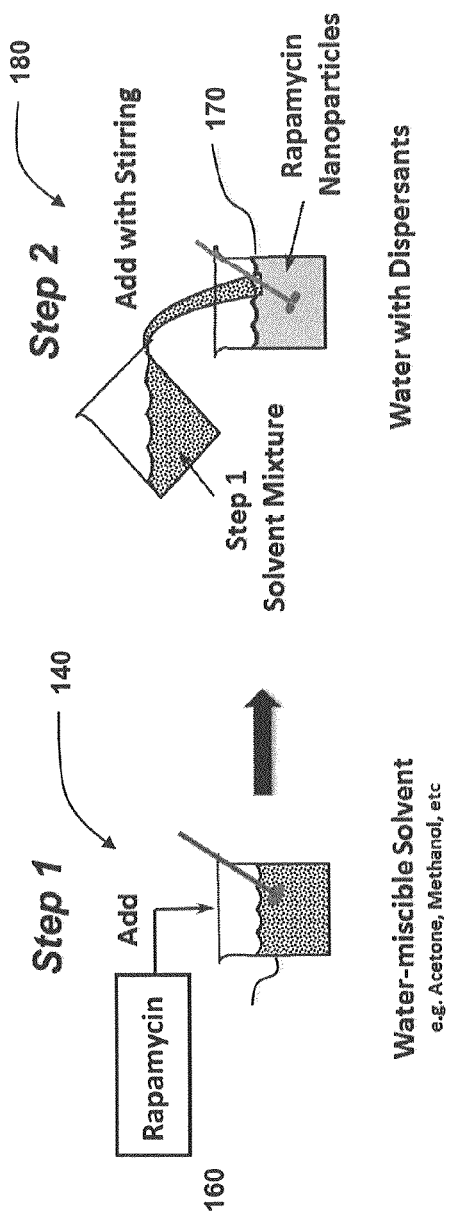
FIG. 3 is a graphic illustration of two basic steps in a preferred process for producing a dispersion of preferred forms of rapamycin nanoparticles according to the teachings of the present invention.

As part of a preferred process for producing microencapsulated rapamycin nanoparticles, FIGS. 2 and 3 illustrate basic preferred steps for producing a dispersion of preferred rapamycin nanoparticles through controlled precipitation. Rapamycin itself (sometimes referred to as "raw" or "neat" rapamycin) is available in powder forms from multiple sources readily identifiable to those in the field. Although rapamycin is not readily soluble in water, solubility can be achieved in some aqueous miscible solvents.

Step 1 in FIG. 3 illustrates a first basic step in the preferred process of producing preferred rapamycin nanoparticles, whereby raw rapamycin is mixed and dissolved into an aqueous miscible solvent 160 (the mixture represented by 140 in FIG. 1). As illustrated by Step 2 in FIG. 3, the resultant solvent mixture is injected into rapidly stirred water containing an appropriate aqueous soluble dispersant 110, preferably sodium cholate, which is a polar amphipathic molecule that tends to form micelles from solution.

After mixing the solvent mixture with the micelle-producing aqueous dispersant 110 in Step 2, the effects of solubility cause the rapamycin to partition to the hydrophobic micelle cores 130. Appropriate solvents 160 and dispersants 110 are discussed in greater detail below. Although the core of the micelles 130 is relatively hydrophobic, which tends to attract the rapamycin from the solvent mixture, the results create a nanoparticle 150 having an outer surface decorated with hydrophilic ends of sodium cholate, which tend to keep the resulting nanoparticles in suspension within the final mixture.

Figure 4:
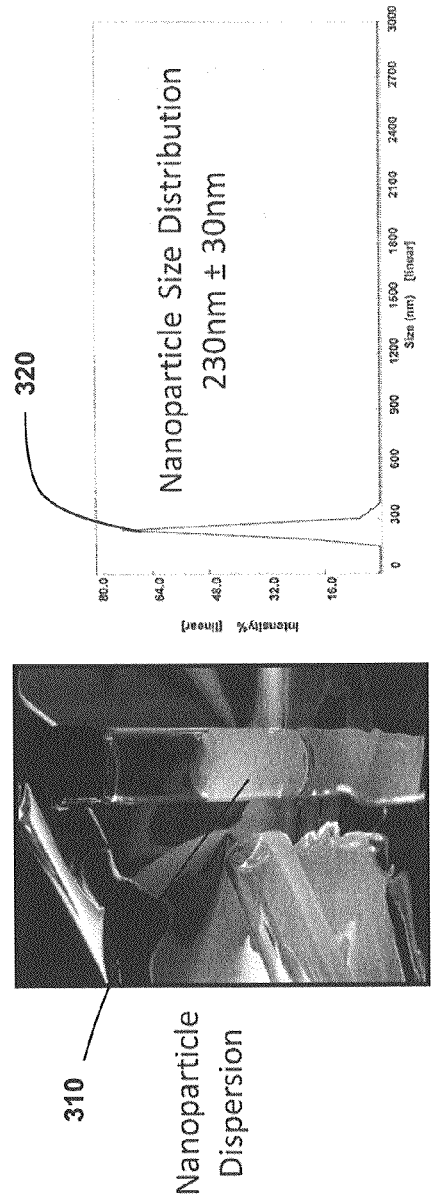
FIGS. 4A and 4B provide a photograph of a dispersion of rapamycin nanoparticles produced as a result of Step 2 in the preferred process illustrated in FIG. 3, together with a graph of nanoparticle size distribution for the particular dispersion shown in the photograph.

A sample of a rapamycin nanoparticle dispersion 310 resulting from Step 2 is shown in the photograph in FIG. 4A. Alongside the photograph, a representative graph 320 is also provided in FIG. 4B. In particular, graph 320 graphically shows one non-limiting example of the resultant rapamycin nanoparticle size distribution in sample 310, as indicated by the intensity of light (the vertical, ordinate axis in the graph) that is scattered by corresponding particle sizes (particle size being plotted as the horizontal abscissa axis in the graph) within the sample dispersion 310. These results are merely one example from one particular embodiment prepared according to the methods described in more detail below. Preparation according to the methods described herein may result in size distributions which may differ from the size distribution illustrated in FIG. 4B, with those possible other particle size distributions considered as being within the scope of the present invention. The use of sodium cholate as taught results in a hydrophilic surface, stabilizing the nanoparticles in the aqueous media, and thereby preventing aggregation and particle growth. Alternative embodiments are also contemplated which use other amphoteric compounds as micelle-inducing compounds. The resulting nanoparticle products, as represented by sample 310, have properties that ensure enhanced and prolonged rapamycin stability—i.e., improved resistance to moisture degradation and/or oxidation for the final product—as well as good intestinal bioabsorption characteristics for the rapamycin protected in this manner.

Rapamycin nanoparticles prepared by controlled precipitation methods can be stabilized against irreversible aggregation, Ostwald ripening, and/or reduced dispersibility, by control of colloid chemistry, particle surface chemistry and particle morphology. For example, nanoparticles prepared by antisolvent solidification can be stabilized by ionic and nonionic surfactants that adsorb to nanoparticle surfaces and promote particle colloid stability through either charge repulsion or steric hindrance, respectively. Moreover, stabilizers can affect nanoparticle crystallinity, which may be preferred to promote different biodistribution and bioavailability in certain indications.

Rapamycin nanoparticles can consist of molecular rapamycin bound by suitable methods to other nanoparticles. Suitable methods of attaching rapamycin to a nanoparticle carrier or substrate may include physical adsorption through hydrogen van der Waals forces or chemisorption through covalent or ionic bonding. Nanoparticle substrates may be either natural or synthetic, and modified to promote specific interactions with rapamycin. Natural nanoparticles include albumin and other proteins, and DNA. Synthetic nanoparticles include organic and inorganic particulates, micelles, liposomes, dendrimers, hyperbranched polymers, and other compounds.

The rapamycin nanoparticles can be processed by any suitable method, such as by milling, high pressure atomization, or rapid anti-solvent precipitation. Milling is suitable provided care is taken to minimize both rapamycin degradation and particle agglomeration. Rapamycin degradation can be reduced with the aid of cooling or cryogenic processes. Agglomeration due to the increased surface area and concomitant adhesive forces can be reduced by the use of dispersants 110 during the milling process.

The individual rapamycin nanoparticles are preferably sized in the range between about 1 nanometer and about 1 micron. Smaller sized rapamycin nanoparticles are preferred, preferably at less than 1 micron diameter, for various reasons, including better control of final particle size, improved stability within the particles, and the ability to tune bioavailability by controlling the crystallinity and composition of the rapamycin nanoparticles.

Manufacturing approaches for the encapsulated rapamycin nanoparticle drug delivery structure embodiments of the present invention include creating a solution of the controlled-release matrix, with the rapamycin nanoparticles dispersed therein, in appropriate proportion and producing a heterogeneous mixture. The solvent for such mixtures can be a suitable volatile solvent for the controlled-release matrix, although it is preferred the solvent be either a poor solvent or non-solvent for the rapamycin nanoparticles so that when the rapamycin nanoparticles are dispersed into the controlled-release matrix solution they remain as discrete nanoparticles. The resulting dispersion of rapamycin nanoparticles in the controlled-release matrix solution can then be reduced to a dry particulate powder by a suitable process, thereby resulting in microparticles of a heterogeneous nature comprised of rapamycin nanoparticles randomly distributed in the controlled-release matrix. The particulate powder may also be tailored by a suitable process to achieve a preferred particle size for subsequent preparation, which may be from about 20 to about 70 microns in diameter.

The rapamycin nanoparticles are microencapsulated with the controlled-release matrix using a suitable particle-forming process to form the encapsulated rapamycin nanoparticle. An example of a particle-forming process is spinning disk atomization and drying. For a detailed discussion of the apparatus and method concerning the aforementioned spin disk coating process, this application incorporates by reference US Patent Applications 2011/221337 and 2011/220430, respectively. Alternatively, for example, the encapsulated rapamycin nanoparticles can be prepared by spray drying.

In some embodiments, not all of the rapamycin nanoparticles will be encapsulated within the controlled-release matrix. Instead the rapamycin nanoparticles may be enmeshed with the controlled-release matrix, with some of the rapamycin nanoparticles wholly contained within the controlled-release matrix while other rapamycin nanoparticles are apparent on the surface of the drug delivery structure, constructed in appearance similar to a chocolate chip cookie.

Depending on the size of the rapamycin nanoparticles, the encapsulated rapamycin nanoparticles are preferably of diameter between 10 and 50 microns, although diameters as large as 75 microns may be suitable for alternatives with corresponding compromises due to the larger size.

The controlled-release matrix of the encapsulated rapamycin nanoparticles can be selected to provide preferred release characteristics of the encapsulated rapamycin nanoparticles. For example, the matrix may be pH sensitive to provide either gastric release, or preferably, enteric release of the rapamycin. Enteric release of the rapamycin is preferred to achieve improved absorption and bioavailability of the rapamycin. Many materials suitable for enteric release are known in the art, including fatty acids, waxes, natural and synthetic polymers, shellac, and other materials. Polymers are a preferred enteric coating and may include copolymers of methacrylic acid and methyl methacrylate, copolymers of methyl acrylate and methacrylic acid, sodium alginate, polyvinyl acetate phthalate, and various succinate or phthalate derivatives of cellulose and hydroxypropyl methylcellulose. Synthetic polymers, such as copolymers of methacrylic acid and either methyl acrylate or methyl methacrylate, are preferred enteric release polymers due to the ability to tune the dissolution pH range of these synthetic polymers by adjusting their comonomer compositions. Examples of such pH sensitive polymers are EUDRAGIT® polymers (Evonik Industries, Essen, Germany). Specifically, EUDRAGIT® S 100, a methyl methacrylate and methacrylic acid copolymer with comonomer ratio of 2:1, respectively, has a dissolution pH of about 7.0, thereby making it suitable for enteric release of rapamycin. More particularly, the methyl methacrylate and methacrylic acid copolymer is essentially insoluble at pH below 7 and dissolves in neutral to basic conditions (pH of about 7 or greater).

The encapsulated rapamycin nanoparticles may be delivered in various physical entities including a pill, tablet, or capsule. The encapsulated rapamycin nanoparticles may be pressed or formed into a pellet-like shape and further encapsulated with a coating, for instance, an enteric coating. In another embodiment, the encapsulated rapamycin nanoparticles may be loaded into a capsule, also further enterically coated.

Various performance enhancing additives can be added to the encapsulated rapamycin nanoparticles. For example, additives that function as free radical scavengers or stabilizers can be added to improve oxidative and storage stability of the encapsulated rapamycin nanoparticles. Free radical scavengers are preferably chosen from the group that consists of glycerol, propylene glycol, and other lower alcohols. Additives alternatively incorporate antioxidants, such as α-tocopherol (vitamin E), citric acid, EDTA, α-lipoic acid, or the like.

Methacrylic acid copolymers with methyl acrylate or methyl methacrylate are moderate oxygen barriers. Furthermore, these polymers will exhibit an equilibrium moisture content. Oxygen transport due to residual solvent, moisture or other causes, can lead to degradation of the encapsulated rapamycin nanoparticles. Oxygen barrier materials can be added to the encapsulated rapamycin nanoparticles formulation to improve oxygen barrier properties. Preferred oxygen barrier polymers compatible with the preferred polymers are polyvinyl alcohol (PVA) and gelatin.

Preferred Microparticle and Nanoparticle Embodiments

Preferred embodiments with rapamycin nanoparticle inclusions comprise discrete nanoparticles of rapamycin heterogeneously dispersed in a controlled-release matrix. As illustrated in accompanying drawings, the rapamycin nanoparticles are prepared by a suitable method and may contain additives to promote nanoparticle stability, modify rapamycin crystallinity, or promote compatibility of the rapamycin nanoparticles with the controlled-release matrix. The controlled-release matrix is formulated to promote release of rapamycin to specific parts of the body, such as the intestine, to enhance oxidative and storage stability of the encapsulated rapamycin nanoparticles, and to maintain the discrete, heterogeneously distributed nature of the rapamycin nanoparticles.

Rapamycin nanoparticles are preferably prepared by antisolvent precipitation or solidification, also sometimes referred to as controlled precipitation or solidification. Antisolvent solidification is a preferred approach as it provides exquisite control of particle size and distribution, particle morphology, and rapamycin crystallinity. For example, it is possible to prepare nanoparticles with narrow particle size distribution that are amorphous, crystalline, or combinations thereof. Such properties may exhibit additional benefits, by further controlling the biodistribution and bioavailability of rapamycin in specific indications.

Rapamycin is dissolved in a suitable water-miscible solvent 160 and then rapidly injected into rapidly stirred water containing an appropriate aqueous soluble dispersant 110. Water-miscible solvents 160 for rapamycin include methanol, ethanol, isopropyl alcohol, acetone, dimethylsulfoxide, dimethylacetamide, n-methylpyrolidone, tetrahydrofuran, and other solvents. Low boiling point, high vapor pressure water-miscible solvents 160 are preferred to facilitate their removal during subsequent microparticle formation. Some preferred water-miscible solvents 160 are methanol, acetone, and isopropyl alcohol. A preferred water-miscible solvent 160 is methanol. Some aqueous soluble dispersants 110 include ionic surfactants such as sodium dodecyl sulfate and sodium cholate, non-ionic surfactants such as Pluronics, Poloxomers, Tweens, and polymers, such as polyvinyl alcohol and polyvinylpyrolidone. Some preferred aqueous-soluble dispersants 110 are sodium cholate, Pluronic F-68, and Pluronic F-127. A preferred aqueous-soluble dispersant 110 is sodium cholate, which provides surprisingly beneficial properties in the present application.

Not only is sodium cholate a surfactant and a dispersant, it serves to produce multimolecular structures which tend to cause aggregation of rapamycin within those structures, particularly when the pH and other condition of the aqueous solution are controlled to allow aggregation of the rapamycin from that aqueous solution. The resulting process allows for rapamycin nanoparticle production that not only tends to produce nanoparticles in highly predictable size ranges, but also provides a resulting nanoparticle with surprisingly desirable levels of colloidal stability. Moreover, while sodium cholate tends to be a polar molecule as well as an amphoteric surfactant, it induces an ionic charge in each hydrophilic nanoparticle when it is enmeshed in the EUDRAGIT® matrix. It is believed that when the nanoparticle is released from the EUDRAGIT® matrix within the animal subject's enteric passages where conditions are basic, the same properties cause the nanoparticle to be more readily received and absorbed through the intestinal walls.

Rapamycin is dissolved in the water-miscible solvent 160 at a concentration of about 0.01% w/v to about 15% w/v, preferably about 0.1% w/v to about 1.0% w/v. The aqueous-soluble dispersant 110 is dissolved in water at a concentration above its critical micelle concentration, or CMC, typically at about 1 to about 10 times the CMC. The rapamycin solution is injected into the aqueous-soluble dispersant solution with agitation at a volumetric ratio of about 1:10 to about 1:1, preferably about 1:5 to about 1:1.

The controlled-release matrix is prepared from a water-soluble polymer, preferably a copolymer of methacrylic acid with either methyl acrylate or methyl methacrylate, such as those marketed under the trade name of EUDRAGIT® and having pH-dependent dissolution properties. More preferably the controlled-release matrix is comprised of EUDRAGIT® S 100, although other water-soluble enteric controlled release matrices would be suitable. Water-soluble controlled-release matrices are selected so as either not to compromise the integrity of rapamycin nanoparticles or to provide a medium in which rapamycin nanoparticles may be prepared by the controlled precipitation methodology described previously.

In the preparation of the water-soluble polymer, it is preferable to maintain conditions that do not compromise the integrity of the rapamycin nanoparticles. Firstly, since the rapamycin nanoparticles are susceptible to solubilization by certain co-solvents, it is important to maintain a suitable quantity of certain co-solvents to achieve controlled-release matrix solubility while not deleteriously affecting the morphology of the rapamycin nanoparticles. Secondly, rapamycin nanoparticles will be susceptible to chemical degradation by high pH; therefore, it is important to modulate the controlled-release matrix solution pH so that rapamycin is not chemically altered. It is preferable that the controlled-release matrix solution pH be maintained below about pH 8. Lastly, it is preferable to achieve nearly complete to complete solubilization of the controlled-release matrix in solution so that microencapsulation of the rapamycin nanoparticles by the controlled-release matrix in subsequent processing steps may proceed with high efficiency. When using the EUDRAGIT® S 100 as the controlled-release matrix, it is preferable to achieve a controlled-release matrix solution by using a combination of co-solvents and solution pH modulation. It is preferable the co-solvents be about 40% or less by volume. Similarly, it is preferable that the pH of the controlled-release matrix solution be about 8 or less, such that the EUDRAGIT® S 100 is not completely neutralized and is preferably only about 80% or less neutralized. These preferred conditions achieve nearly complete to complete solubilization of the EUDRAGIT® S 100 in a medium that is mostly aqueous and that maintains the integrity of the rapamycin nanoparticles, therefore leading to their microencapsulation by the controlled-release matrix in subsequent processing steps.

The rapamycin nanoparticles prepared by the preferred controlled precipitation method are added to the aqueous solution of the controlled-release matrix, resulting in a nanoparticle dispersion in the solubilized controlled-release matrix. Alternatively, the rapamycin solubilized in a suitable or preferred co-solvent can be dispersed into the aqueous solution of the controlled-release matrix leading to controlled precipitation of rapamycin particles, thereby leading to a rapamycin nanoparticle dispersion in fewer processing steps, but of appropriate composition to permit subsequent microencapsulation processing.

As an alternative embodiment, the encapsulated rapamycin nanoparticles are created using pre-existing nanoparticle substrates, such as albumin, to create, in the case of albumin, "albumin-rapamycin nanoparticles." Within this general class of alternatives, preferred approaches for creating the albumin-rapamycin nanoparticles involve encapsulating rapamycin within albumin nanoparticles or preferentially associating rapamycin with albumin nanoparticles through physical or chemical adsorption. The albumin nanoparticles themselves are preferably formed from human serum albumin, a plasma protein derived from human serum.

More particularly, this embodiment preferably involves use of a therapeutic peptide or protein that is covalently or physically bound to albumin, to enhance its stability and half-life. With the albumin stabilized, the rapamycin is mixed with the stabilized albumin in an aqueous solvent and passed under high pressure to form rapamycin-albumin nanoparticles in the size range of 100-200 nm (comparable to the size of small liposomes).

Preferred embodiments also address degradation risks and other limits imposed by the related art by preparing encapsulated rapamycin nanoparticles as a heterogeneous mixture of rapamycin nanoparticles in a polymer matrix. Distributed nanoparticles are morphologically different than homogeneous rapamycin and are less susceptible to degradation because of the bulk nature of the nanoparticles compared to the smaller size of molecular rapamycin.

Another alternative embodiment involves biodegradable polymers loaded with rapamycin. Biodegradable polymers loaded with drugs can be microparticles. "Microparticle" refers to particles between about 0.1 and 300 μm in size. Drug-loaded biodegradable polymers release the drug in a time-dependent manner.

As used herein, "biodegradable" refers to any natural means by which a polymer can be disposed of in a patient's body. This includes such phenomena as, without limitation, biological decomposition, bioerosion, absorption, resorption, etc. Biodegradation of a polymer in vivo results from the action of one or more endogenous biological agents and/or conditions such as, without limitation, enzymes, microbes, cellular components, physiological pH, temperature and the like.

In some aspects, the biodegradable polymers can be poly-ε-caprolactone (PCL) microparticles. PCL is a biodegradable, biocompatible, and semicrystalline polymer. PCL is useful for drug delivery because it is highly permeable to many drugs and is non-toxic. Sinha et al. 2004. Rapamycin can also be loaded onto microparticles of other biodegradable polymers, including but not limited to aliphatic polyester, polylactide, polyglycolide, poly(lactide-co-glycolide), mixtures thereof, and their copolymers. Such biodegradable polymers are known in the art.

Rapamycin may be loaded onto microspheres of PCL alone or of PCL copolymers or blends to obtain the desired drug release characteristics. Copolymers of PCL can be formed using many different monomers, including, but not limited to, ethyleneoxide, polyvinylchloride, chloroprene, polyethylene glycol, polystyrene, diisocyanates (urethanes), tetrahydrofuran (THF), diglycolide, dilactide, δ-valeractone, substituted caprolactones, 4-vinyl anisole, styrene, methyl methacrylate, and vinyl acetate.

Drug-loaded PCL microspheres can be prepared by several different methods known by persons of skill in the art, including, but not limited to, an o/w emulsion solvent extraction/evaporation method, a w/o/w emulsion solvent evaporation technique, a spray drying technique, a solution-enhanced dispersion method, and a hot melt technique. These methods are described in more detail in Sinha et al., 2004, which is hereby incorporated by reference. Briefly, as a non-limiting example, the o/w emulsion solvent extraction evaporation method can be performed by dissolving the required amount of polymer and drug in an organic phase, emulsifying under stirring with polyvinyl alcohol to form an o/w emulsion, stirring for 3 hours at about 500 rpm to evaporate the organic phase, and filtering and drying the formed microspheres.

Drug-loaded microspheres of aliphatic polyesters, polylactide, polyglycolide, and poly(lactide-co-glycolide) can be prepared by several different methods known by persons of skill in the art. Non-limiting examples can be found in the following references, all of which are hereby incorporated by reference: Kemala at al., 2012; Ghassemi et al., 2009; Corrigan & Heelan, 2001; Cleland et al., WIPO Pub. No. WO 1995/11009; and Atkins et al., WIPO Pub. No. WO 1995/009613.

In some aspects of this alternative embodiment, the microparticles loaded with rapamycin are encased, encapsulated, or coated to provide for release in the intestinal tract, including the colon.

In some aspects, the microparticles are coated with an enteric coating, which is a coating that prevents release and absorption of active ingredients until they reach the intestine. Some enteric coatings facilitate delivery of agents to the colon. In some embodiments, the enteric coating is a EUDRAGIT® coating. EUDRAGIT® coatings include EUDRAGIT® L 100-55, Poly(methacrylic acid-co-ethyl acrylate) 1:1; EUDRAGIT® L 30 D-55, Poly(methacrylic acid-co-ethyl acrylate) 1:1; EUDRAGIT® L-100, Poly (methacrylic acid-co-methyl methacrylate) 1:1; EUDRAGIT® S 100, Poly(methacrylic acid-co-methyl methacrylate) 1:2; EUDRAGIT® FS 30 D, Poly(methyl acrylate-co-methyl methacrylate-co-methacrylic acid) 7:3:1; EUDRAGIT® RL, Poly(ethyl acrylate-co-methyl methacrylate-co-trimethylammonioethyl methacrylate chloride) 1:2:0.2; EUDRAGIT® RS, Poly(ethyl acrylate-co-methyl methacrylate-co-trimethylammonioethyl methacrylate chloride) 1:2:0.1; and EUDRAGIT® E, Poly(butyl methacrylate-co-(2-dimethylaminoethyl) methacrylate-co-methyl methacrylate) 1:2:1. Other coatings include EUDRAGIT® RS, EUDRAGIT® RL, ethylcellulose, and polyvinyl acetate. Benefits include pH-dependent drug release, protection of active agents sensitive to gastric fluid, protection of gastric mucosa from active agents, increase in drug effectiveness, good storage stability, and GI and colon targeting, which minimizes risks associated with negative systemic effects and maintains effective dosing.

In some aspects, colon targeting of rapamycin can be achieved by creating PCL microparticles loaded with rapamycin or rapamycin analog and subsequently coating the microparticles with EUDRAGIT® S 100. Methods of making such coated microparticles can be found in Ghorab et al., 2011, which is hereby incorporated by reference. Briefly, drug-loaded PCL microparticles are suspended in a solution containing an appropriate amount of EUDRAGIT® S 100 dissolved in ethyl alcohol. The suspension is poured into distilled water. The resulting mixture is homogenized for five minutes and then mechanically stirred until the organic solvent is completely evaporated. Microparticles are collected, washed with cyclohexane twice, and dried overnight in a desiccator.

Some other examples of enteric coating components include cellulose acetate phthalate, methyl acrylate-methacrylic acid copolymers, cellulose acetate succinate, hydroxypropyl methylcellulose phthalate, hydroxypropyl methylcellulose acetate succinate, polyvinyl acetate phthalate, methyl methacrylate-methacrylic acid copolymers, sodium alginate, and stearic acid. The coating may include suitable hydrophilic gelling polymers including, but not limited to, cellulosic polymers, such as methylcellulose, carboxymethylcellulose, hydroxypropylcellulose, hydroxypropylmethylcellulose, hydroxyethylcellulose, and the like; vinyl polymers, such as polyvinylpyrrolidone, polyvinyl alcohol, and the like; acrylic polymers and copolymers, such as acrylic acid polymer, methacrylic acid copolymers, ethyl acrylate-methyl methacrylate copolymers, natural and synthetic gums, such as guar gum, arabic gum, xanthan gum, gelatin, collagen, proteins, polysaccharides, such as pectin, pectic acid, alginic acid, sodium alginate, polyaminoacids, polyalcohols, polyglycols, and the like; and mixtures thereof. Any other coating agent known to those of ordinary skill in the art is contemplated for inclusion in the coatings of the microcapsules set forth herein.

The coating may optionally comprise a plasticizer, such as dibutyl sebacate, polyethylene glycol and polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol or a combination thereof. The coating may optionally include a gum. Non-limiting examples of gums include homopolysaccharides such as locust bean gum, galactans, mannans, vegetable gums such as alginates, gum karaya, pectin, agar, tragacanth, acacia, carrageenan, chitosan, alginic acid, other polysaccharide gums (e.g., hydrocolloids), acacia *catechu*, salai guggal, indian bodellum, sopaiba gum asafetida, cambi gum, *Enterolobium cyclocarpum*, mastic gum, benzoin gum, sandarac, gambier gum, butea *frondosa* (Flame of Forest Gum); myrrh, konjak mannan, guar gum, welan gum, gellan gum, tara gum, locust bean gum, carrageenan gum, glucomannan, galactan gum, sodium alginate, xanthan gum deacetylated xanthan gum, pectin, sodium polypectate, gluten, karaya gum, tamarind gum, ghatti gum, Acaroid/Yacca/Red gum, dammar gum, juniper gum, ester gum, ipil-ipil seed gum, gum talha (acacia seyal), and cultured plant cell gums including those of the plants of the genera: *Acacia, Actinidia, Aptenia, Carbobrotus, Chickorium, Cucumis, Glycine, Hibiscus, Hordeurn, Letuca, Lycopersicon, Malus, Medicago, Mesembryanthemum, Oryza, Panicum, Phalaris, Phleum, Poliathus, Polycarbophil, Sida, Solanum, Trifolium, Trigonella, Afzelia africana* seed gum, *Treculia africana* gum, detarium gum, *cassia* gum, carob gum, *Prosopis africana* gum, *Colocassia esulenta* gum, *Hakea gibbosa* gum, khaya gum, scleroglucan, *zea*, mixtures of any of the foregoing, and the like.

A variety of other encasing materials and systems for delivering rapamycin-loaded biodegradable microspheres to the colon can be used alone or in combination with a pH-dependent coating like EUDRAGIT® S 100. Non-limiting examples follow.

Hydrophilic gelling polymers or copolymers can be included in a material encasing one or more microspheres to provide a time-dependent release of drug-loaded microspheres. Non-limiting examples of hydrophilic gelling copolymers include methylcellulose, carboxymethylcellulose, hydroxypropylcellulose, hydroxypropyl methylcellulose, carbomers, polyvinyl alcohols, polyoxyethylene glycols, polyvinylpyrrolidones, poloxamers, or natural or synthetic rubbers. An intermediate layer of these polymers can be included to delay release of active ingredient for a desired amount of time, as described in Poli et al., (EP0572942). Another example of a time-dependent encasing material is a wax matrix including, for example, behenic acid, as described in Otuska & Matsuda, 1994.

Polysaccharides that are resistant to digestive enzymes but are enzymatically broken down by bacteria in the colon can be included in an encasing material. Non-limiting examples include chitosan and pectin as described in Coulter (EP2380564), and azopolymers, disulfide polymers, amylose, calcium pectinate, and chondroitin sulfate as described in Watts (EP0810857).

A starch capsule coated with an enteric coating such as EUDRAGIT® S 100 or EUDRAGIT® L 100 may be used, as described in Watts (EP0180857). A variety of starches, including modified starches and starch derivatives may be used. Non-limiting examples include hydroxyethyl starch, hydroxypropyl starch, carboxymethyl starch, cationic starch, acetylated starch, phosphorylated starch, succinate derivatives, or grafted starches.

A layer of insoluble or relatively insoluble rupturable polymer can be used as part of a strategy to provide for abrupt release of drug-loaded microspheres in the colon. The rupturable polymer can comprise one or more of a variety of suitable polymers known by those of skill in the art, including, but not limited to, cellulose acetate, cellulose acetate propionate, or ethyl cellulose. A variety of strategies for causing rupture of the polymer in the colon can be employed. As a non-limiting example, the rupturable polymer can be designed to rupture upon encountering increased pressure due to intestinal peristalsis, as described in Muraoka et al., 1998. As another example, the rupturable polymer can be semi-permeable, and an effervescent solid can be included in a core containing the drug-loaded microparticles, as described in Krogel & Bodmeier, 1999. As another example, a layer of swellable material, including, but not limited to, croscarmellose sodium or hydroxypropyl methylcellulose, can be disposed within the rupturable polymer layer, as described in Bussemer et al., 2001. Controlled entry of water past the rupturable polymer layer can be provided by embedded hydrophilic particulate material, as described in Lerner et al., (WIPO Pub. No. WO 1999/018938).

A two-piece encasing system, as described in McNeill et al., (WIPO Pub. No. WO 1990/009168) can be used to provide for release of drug-loaded microspheres in the colon. One of the pieces is a relatively water insoluble capsule with an open orifice, which is covered by a second piece that swells as it takes up water. The swelling causes displacement from the orifice and release of the capsule contents.

Examples of Preferred mTOR Inhibiting Preparations

Example 1

Development of methods to produce rapamycin nanoparticles. Rapid solvent exchange was used to examine the formation of rapamycin nanoparticles. Three water-miscible solvents 160 and three water-soluble surfactants were selected to study their respective effects on the formation and morphology of rapamycin nanoparticles. The water-miscible solvents 160 were isopropyl alcohol (Solvent 1), acetone (Solvent 2), and methanol (Solvent 3). The water-soluble surfactants were Pluronic F-68 (Dispersant 1, a non-ionic PEO-PPO-PEO block copolymer), Pluronic F-127 (Dispersant 2, a non-ionic PEO-PPO-PEO block copolymer), and sodium cholate (Dispersant 3, an anionic surfactant). Rapamycin was dissolved in each of the water-miscible solvents 160 at a concentration of 0.25% w/v. The water-soluble surfactants were dissolved in deionized water at concentrations of 0.5% w/v, 0.5% w/v, and 1.0% w/v, respectively, for each of the dispersants. Each experimental combination (e.g. NP-1 to NP-9 in following table) consisted of 5 mL of rapamycin solution and 25 mL of surfactant solution, resulting in a dilution factor of 1:5 solvent:water. 25 mL of surfactant solution was transferred to a 50 mL beaker and stirred with the aid of a magnetic micro stir bar. Rapamycin solution was rapidly injected at 500 µL increments with the aid of a micropipette with the pipette tip placed below the surface of the rapidly stirred surfactant solution. The visual appearance of the resulting nanoparticles and their colloidal stability after 24-hours were qualitatively assessed. The following table summarizes the qualities of the rapamycin nanoparticle dispersions. Qualitatively, rapamycin nanoparticle dispersions having a colorless to blue, opalescent appearance will have particle sizes on the order of less than about 300 nm as evidenced by their interaction with the ultraviolet wavelengths of visible light. Whereas, dispersions having a more white appearance will have particle sizes larger than about 300 nm due to their interaction with the broader spectrum of visible light. Rapamycin nanoparticle formulations NP-7 and NP-9 were selected as preferred methods of nanoparticle preparation.

|  | Dispersant 1 | Dispersant 2 | Dispersant 3 |
| --- | --- | --- | --- |
| Solvent 1 | NP-1: White, settled, resdispersible | NP-2: Blue, opalescent, settled, redispersible | NP-3: Clear, aggregated, redispersible |
| Solvent 2 | NP-4: Blue, opalescent, some settling | NP-5: White, settled, redispersible | NP-6: Blue, opalescent, settled, redispersible |
| Solvent 3 | NP-7: Blue, opalescent, stable | NP-8: Blue to white, settled, redispersible | NP-9: Blue, opalescent, stable |

Example 2

Preparation of a high-concentration rapamycin nanoparticle dispersion. The water-miscible solvent 160 and water-soluble dispersant 110 of NP-9 from Example 1 was used to prepare rapamycin nanoparticles. 656 mg of rapamycin were dissolved in 6.56 mL of Solvent 3 to yield a 1.0% w/v solution. This volume of rapamycin solution was injected into 26.25 mL of 1.0% w/v Dispersant 1 in deionized water. The resulting rapamycin nanoparticle dispersion had a final rapamycin content of 2.4% w/w. As a non-limiting example, the particle size of the particular dispersion was determined by dynamic light scattering to be $D_{50}$=230 nm with a single peak according to this preparation method. Other particle sizes may be observed when utilizing the described preparation method, and those sizes would still be within the scope of the present invention.

Example 3

Preparation of a water-soluble enteric coating. 3.5 g of EUDRAGIT® S 100 were added to 70 mL of deionized water with light stirring, resulting in a white dispersion. 1.4 g of sodium hydroxide were added to the dispersion with continued stirring. The resulting dispersion gradually turned clear and colorless indicating an aqueous solution of EUDRAGIT® S 100. The estimated concentration of sodium hydroxide was 0.5M.

Example 4

Preparation of a feedstock containing rapamycin nanoparticles and a water-soluble enteric coating. Rapamycin nanoparticles were prepared as described in Example 2 and then slowly added to an aqueous solution of EUDRAGIT® S 100 prepared as in Example 3. The ratio of rapamycin to EUDRAGIT® S 100 was 1:9, or 10% wt. rapamycin payload. The resulting dispersion was allowed to stir for several minutes to observe stability. After one hour, the dispersion had transformed to a clear yellow, indicating destruction of the rapamycin nanoparticles and a change in the rapamycin. Addition of a small amount of acetic acid to reduce the solution pH to below neutral resulted in a clear, colorless solution.

Example 5

Preparation of water-soluble enteric coating with a water-miscisble co-solvent. 3.5 g of EUDRAGIT® S 100 were added to 30/70 v/v methanol/deionized water, resulting in a white dispersion. The dispersion was stirred continuously until a clear solution was formed.

Example 6

Preparation of a feedstock containing rapamycin nanoparticles and a water-soluble enteric coating. Rapamycin nanoparticles were prepared as described in Example 2 and then slowly added to an aqueous solution of EUDRAGIT® S 100 prepared as in Example 5. The ratio of rapamycin to EUDRAGIT® S 100 was 1:9, or 10% wt. rapamycin payload. The white dispersion was allowed to stir for several minutes after which the dispersion was transformed into a clear solution indicating the rapamycin nanoparticles had been destroyed.

Example 7

Preparation of a partially-neutralized, water-soluble enteric coating with a water-miscible co-solvent. 3.5 g of EUDRAGIT® S 100 were added to 10/90 v/v methanol/deionized water, resulting in a white dispersion. The dispersion was titrated to clarity with 2.000 mL of 4.8M sodium hydroxide. The estimated neutralization of the EUDRAGIT® S 100 was 78%.

Example 8

Preparation of a feedstock containing rapamycin nanoparticles and a water-soluble enteric coating. Rapamycin nanoparticles were prepared as described in Example 2 then slowly added to an aqueous solution of EUDRAGIT® S 100 as prepared in Example 7. The ratio of rapamycin to EUDRAGIT® S 100 was 1:9, or 10% wt. rapamycin payload. The resulting white dispersion remained stable for several hours as indicated by no change in color or change in optical clarity. The final pH was 7.5. The particle size of the particular final dispersion utilizing this particular preparation method was determined by dynamic light scattering to be $D_{50}$=756 nm with a single peak and indicating possible clustering of the rapamycin nanoparticles in the resulting feedstock. The observed particle size represents one example of the results observed utilizing this particular preparation method, and other particle sizes may be observed in other embodiments which would also be within the scope of the present invention. As will be understood by those of skill in the art, other methods of preparation and/or utilizing various other constituent components or varying the concentration of such components may also result in particle sizes that essentially are the same, larger or smaller than those prepared according to this method.

Example 9

Preparation of a feedstock containing rapamycin nanoparticles and a water-soluble enteric coating. The rapamycin solution used in Example 2 was injected, with stirring, into the aqueous solution of EUDRAGIT® S 100 prepared in Example 7. The ratio of rapamycin to EUDRAGIT® S 100 was 1:9, or 10% wt. rapamycin payload. A blue, opalescent colloid was formed and it remained stable for several hours as indicated by no change in color or change in optical clarity. The final pH was 7.5. The particle size of the particular final dispersion was determined by dynamic light scattering to be $D_{50}$=305 nm with a single peak. As indicated above, this observed particle size is presented merely as one example and other sizes may result in other embodiments, such other sizes being within the scope of the present invention.

Example 10

Spray drying of feedstock containing rapamycin nanoparticles and a water-soluble enteric coating. The feedstocks prepared in Examples 8 and 9 were spray dried and analyzed for rapamycin content. Particles prepared from Example 8 had a rapamycin content of 9.5% wt. (87% rapamycin yield). Particles prepared from Example 9 had a rapamycin content of 7.9% wt. (80% rapamycin yield).

Example 11

Storage stability of enteric-coated encapsulated rapamycin nanoparticles. Microparticles prepared by spray drying in Example 10 were stored under controlled conditions at room temperature and 50% relative humidity. Samples were analyzed weekly for rapamycin content. All samples maintained at least 95% of their original rapamycin content at all of the time points for at least three weeks.

Example 12

Figure 5:
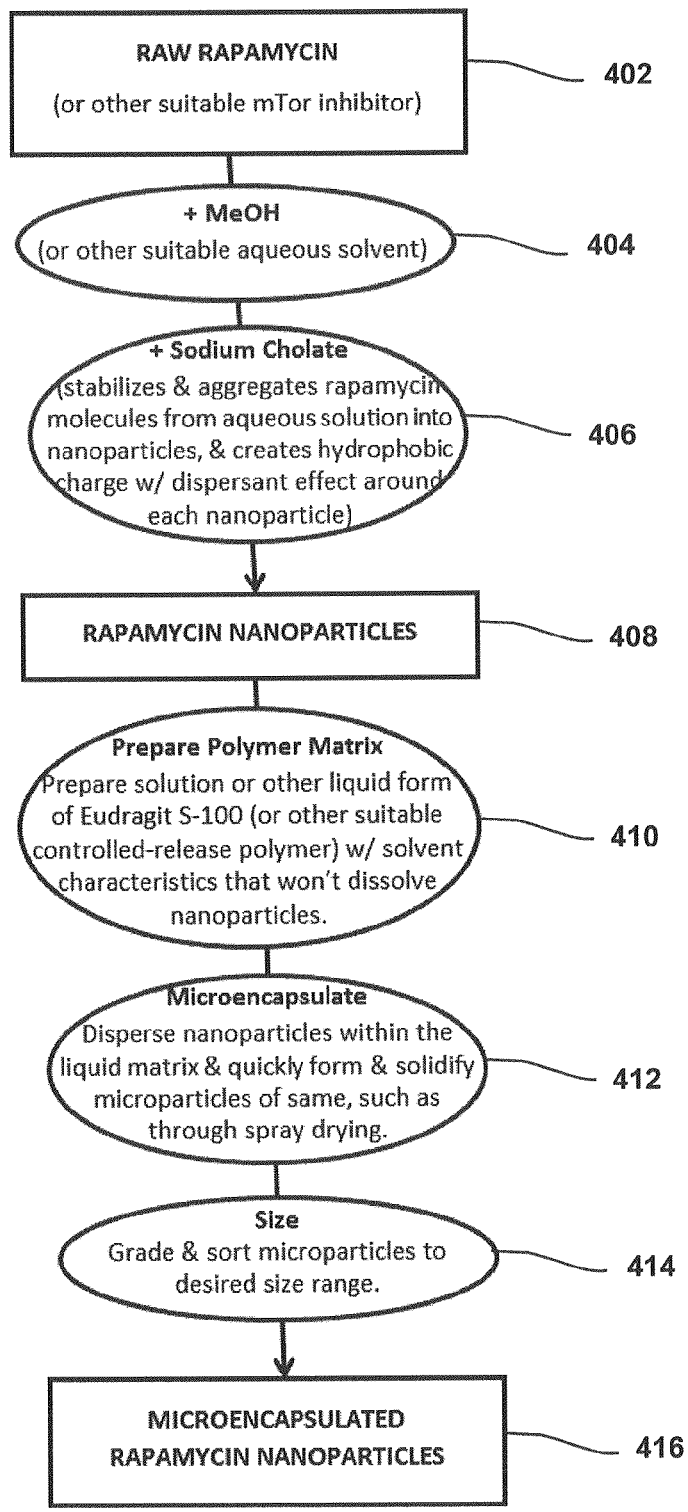
FIG. 5 is a flowchart illustrating detailed steps of a more comprehensive preferred process for producing preferred forms of enteric-coated rapamycin nanoparticles, which includes the process for producing a nanoparticle dispersion as illustrated in FIGS. 2 and 3, together with additional steps for microencapsulating the rapamycin nanoparticles.

Preparation of nanoparticles in EUDRAGIT® S 100 as illustrated in FIG. 5. A rapamycin solution was prepared by combining rapamycin with methanol (at Steps 402 and 404) in a 10% w/v ratio as 3.03 g rapamycin and 30.25 mL methanol. A 1% w/w sodium cholate solution was prepared by combining 1.2 g sodium cholate with 120 mL deionized water (not shown in FIG. 5, but which would necessarily occur at some point prior to Step 406). Nanoparticle formation was achieved by transferring the rapamycin solution with a 60 mL plastic syringe equipped with a 20 ga needle and, injecting the rapamycin solution below the surface of the sodium cholate solution in a 250 mL beaker (Steps 406 and 408). Mixing was accomplished with a paddle mixer operating at 300 rpm yielding a rapamycin nanoparticle suspension. At Step 410, a 10% w/w EUDRAGIT® S 100 solution was prepared by combining 20 g EUDRAGIT® S 100 in a 9.7% w/v mixture with 180 mL deionized water, 25.72 mL methanol in a 12.5% v/v mixture, and 1.8 g sodium cholate in a 0.875% w/v mixture. This 10% w/w EUDRAGIT® S 100 solution was titrated with 4M sodium hydroxide to achieve a pH of between about 7.5 and about 7.6. Encapsulated rapamycin particles were then fabricated by combining the EUDRAGIT® S 100 solution with the rapamycin nanoparticle suspension at Step 412. The EUDRAGIT® S 100 solution and the rapamycin nanoparticle suspension were combined in a 500 mL bottle, adding 2.13 g of glycerol (a glycerin-based compound) and mixing with a magnetic stir bar. The combined EUDRAGIT® S 100 solution and rapamycin nanoparticle suspension were then spray dried and collected. The spray drying parameters (shown at Step 412) included a 0.4 mm nozzle, nozzle air pressure of 3 bar, input air temperature of 110° C., a sample pump rate of 5 mL/min and an air speed of 0.30 m/min. After the preferred nanoparticle microencapsulation process is complete, the nanoparticles may then be graded and sorted according to the desired size range at Step 414. Alternatively, the resulting dispersion of rapamycin nanoparticles in the controlled-release matrix solution can be reduced to a dry particulate powder by a suitable process, thereby resulting in microparticles of a heterogeneous nature comprised of rapamycin nanoparticles randomly distributed in the controlled-release matrix. This dry particulate powder can then be combined with excipients and pressed into tablet form.

Preferred embodiments of the tablet form for oral administration of enteric-coated rapamycin nanoparticles may include between 1 and 3 mg of pharmaceutically active rapamycin, with the tablets preferably constituting approximately 10% by weight of rapamycin although other percentages may be contemplated. The preferred dispersant used is sodium cholate at approximately 10% by weight in the final product. EUDRAGIT® S 100 functions as the enteric release copolymer, preferably at approximately 65% by weight. Sodium hydroxide is preferably used to neutralize the EUDRAGIT® S 100 as previously described, with no sodium hydroxide being present in the final product. Various components may be utilized as excipients in the final preparation as described above. Preferred embodiments preferably use excipients including lactose monohydrate, macrogol or polyethylene glycol (PEG 8000), magnesium stearate, and talc. The amount of each excipient by weight is variable dependent on production of an effective tablet. However, lactose monohydrate and PEG 8000 preferably constitute the bulk of the excipients by weight and percentage in the entire tablet in preferred embodiments, with each constituting 35-50% of the preferred tablet composition. This percentage would equate to approximately 55-70 mg of each of these two components in preferred embodiments. The remaining excipients, magnesium stearate and talc, would constitute less of the final composition, each being approximately 1% by weight of the entire tablet in preferred embodiments.

Alternative methods of preparation include a continuous-flow generation of rapamycin nanoparticles prior to atomizing the particles using a spin disk atomization process or the like. Rather than using the multi-step process as described hereinabove, rapamycin nanoparticles may be produced in a continuous stream, single-phase synthesis.

Methods of Using Rapamycin Compositions

"Treatment" and "treating" refer to administration or application of a therapeutic agent to a subject or performance of a procedure or modality on a subject for the purpose of obtaining a therapeutic benefit for a disease or health-related condition. For example, the rapamycin compositions of the present invention may be administered to a subject for the purpose of treating or preventing FCGS.

The terms "therapeutic benefit," "therapeutically effective," or "effective amount" refer to the promotion or enhancement of the well-being of a subject. This includes, but is not limited to, a reduction in the frequency or severity of the signs or symptoms of a specified malady or group of maladies.

"Prevention" and "preventing" are used according to their ordinary and plain meaning. In the context of a particular disease or health-related condition, those terms refer to administration or application of an agent, drug, or remedy to a subject or performance of a procedure or modality on a subject for the purpose of preventing or delaying the onset of a disease or health-related condition.

Rapamycin compositions, as disclosed herein, including preferably encapsulated rapamycin nanoparticles, may be used to prevent, treat, delay or reduce any disease or condition (or its precursors or sequelae) for which an inhibitor of mTOR is contemplated as effective for treatment, prevention, or delaying or reducing its progression. For example, methods are disclosed herein of using rapamycin compositions to treat or prevent diseases or conditions which a patient has been identified as being at risk for developing, including: feline chronic gingivo-stomatitis (FCGS) and other gum and gingival diseases, and other autoimmune diseases, all of which may occur in humans or other animals.

Pharmaceutical Preparations

Certain methods and compositions set forth herein are directed to administration of an effective amount of a composition comprising the rapamycin compositions of the present invention.

1. Compositions

A "pharmaceutically acceptable carrier": includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated. The compositions used in the present invention may comprise different types of carriers depending on whether it is to be administered in solid, liquid or aerosol form, and whether it needs to be sterile for such routes of administration as injection.

The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions, and these are discussed in greater detail below. For human administration, preparations should meet sterility, pyrogenicity, and general safety and purity standards as required by FDA Office of Biologics standards.

The formulation of the composition may vary depending upon the route of administration. For parenteral administration in an aqueous solution, for example, the solution should be suitably buffered if necessary and the liquid diluent first rendered isotonic with sufficient saline or glucose. In this connection, sterile aqueous media that can be employed will be known to those of skill in the art in light of the present disclosure.

In addition to the compounds formulated for parenteral administration, such as intravenous or intramuscular injection, other pharmaceutically acceptable forms include, e.g., tablets or solids for oral administration; liposomal and nanoparticle formulations; enteric coating formulations; time release capsules; formulations for administration via an implantable drug delivery device; and any other form. One may also use nasal solutions or sprays, aerosols or inhalants in the present invention.

The capsules may be, for example, hard-shell capsules or soft-shell capsules. The capsules may optionally include one or more additional components that provide for sustained release.

In certain embodiments, pharmaceutical composition includes at least about 0.1% by weight of the active compound. In other embodiments, the pharmaceutical composition includes about 2% to about 75% of the weight of the composition, or between about 25% to about 60% by weight of the composition, for example, and any range derivable therein.

The compositions may comprise various antioxidants to retard oxidation of one or more components. Additionally, the prevention of the action of microorganisms can be accomplished by preservatives such as various antibacterial and antifungal agents, including, but not limited to, parabens (e.g., methylparabens, propylparabens), chlorobutanol, phenol, scorbic acid, thimerosal or combinations thereof. The composition should be stable under the conditions of manufacture and storage, and preserved against the contaminating action of microorganisms, such as bacteria and fungi.

In certain preferred embodiments, an oral composition may comprise one or more binders, excipients, disintegration agents, lubricants, flavoring agents, and combinations thereof. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar, EUDRAGIT® Acrylic Drug Delivery Polymers, or any combination thereof.

In particular embodiments, prolonged absorption can be brought about by the use in the compositions of agents delaying absorption, such as, for example, aluminum monostearate, gelatin, EUDRAGIT® Acrylic Drug Delivery Polymers or combinations thereof.

2. Alternative Routes of Administration

Upon formulation, solutions will be administered in a manner compatible with the dosage formulation and in such amount as is therapeutically effective.

Absent clear limitation in a particular context, compositions according to these teachings can be administered to the subject using any method known to those of ordinary skill in the art. For example, a pharmaceutically effective amount of the composition may be administered intravenously, intracerebrally, intracranially, intraventricularly, intrathecally, into the cortex, thalamus, hypothalamus, hippocampus, basal ganglia, substantia nigra or the region of the substantia nigra, cerebellum, intradermally, intraarterially, intraperitoneally, intralesionally, anally, subcutaneously, orally, topically, locally, by inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the foregoing as would be known to one of ordinary skill in the art (Remington's, 1990).

In particular embodiments, the composition is administered to a subject using a drug delivery device. Any drug delivery device is contemplated for use in delivering an effective amount of the inhibitor of mTOR or mTOR Complex 1(mTORC1).

3. Dosage

A pharmaceutically effective amount of an inhibitor of mTOR is determined based on the intended goal. The quantity to be administered, both according to number of treatments and dose, depends on the subject to be treated, the state of the subject, the protection desired, and the route of administration. Precise amounts of the therapeutic agent also depend on the judgment of the practitioner and are peculiar to each individual.

The amount of rapamycin or rapamycin analog or derivative to be administered will depend upon the disease to be treated, the length of duration desired and the bioavailability profile of the implant, and site of administration. Generally, the effective amount will be within the discretion and wisdom of the patient's physician. Guidelines for administration include dose ranges of from about 0.01 mg to about 500 mg of rapamycin or rapamycin analog.

For example, a dose of the inhibitor of mTOR may be about 0.0001 milligrams to about 1.0 milligrams, or about 0.001 milligrams to about 0.1 milligrams, or about 0.1 milligrams to about 1.0 milligrams, or even about 10 milligrams per dose or so. Multiple doses can also be administered. In some embodiments, a dose is at least about 0.0001 milligrams. In further embodiments, a dose is at least about 0.001 milligrams. In still further embodiments, a dose is at least 0.01 milligrams. In still further embodiments, a dose is at least about 0.1 milligrams. In more particular embodiments, a dose may be at least 1.0 milligrams. In even more particular embodiments, a dose may be at least 10 milligrams. In further embodiments, a dose is at least 100 milligrams or higher.

In other non-limiting examples, a dose may also comprise from about 1 microgram/kg-body-weight, about 5 microgram/kg-body-weight, about 10 microgram/kg body weight, about 50 microgram/kg-body-weight, about 100 microgram/kg body weight, about 200 microgram/kg-body-weight, about 350 microgram/kg body weight, about 500 microgram/kg-body-weight, about 1 milligram/kg body weight, about 5 milligram/kg-body-weight, about 10 milligram/kg body weight, about 50 milligram/kg body weight, about 100 milligram/kg body weight, about 200 milligram/kg-body-weight, about 350 milligram/kg body weight, about 500 milligram/kg body weight, to about 1000 mg/kg body weight or more per administration, and any range derivable therein. In non-limiting examples of a derivable range from the numbers listed herein, a range of about 5 mg/kg-body-weight to about 100 mg/kg-body-weight, about 5 microgram/kg-body-weight to about 500 milligram/kg-body-weight, etc., can be administered, based on the numbers described above.

The dose can be repeated as needed as determined by those of ordinary skill in the art. Thus, in some embodiments of the methods set forth herein, a single dose is contemplated. In other embodiments, two or more doses are contemplated. In some embodiments, the two or more doses are the same dosage. In some embodiments, the two or more doses are different dosages. Where more than one dose is administered to a subject, the time interval between doses can be any time interval as determined by those of ordinary skill in the art. For example, the time interval between doses may be about 1 hour to about 2 hours; about 2 hours to about 6 hours; about 6 hours to about 10 hours; about 10 hours to about 24 hours; about 1 day to about 2 days; about 1 week to about 2 weeks, or longer, or any time interval derivable within any of these recited ranges. In specific embodiments, the composition may be administered daily, weekly, monthly, annually, or any range therein.

Doses for encapsulated rapamycin (enteric-coated rapamycin) and for encapsulated rapamycin nanoparticles may be different. According to preferred embodiments of the present invention, doses of the mTOR inhibitor are contemplated in a dosage range of between one microgram/kilogram and eight hundred micrograms/kilogram of the subject's weight. More particular dosage ranges for preferred embodiments are between about 50 micrograms and up to about 200 micrograms per kilogram for daily administration, or the equivalent for other frequencies of administration.

Although dosing may vary based on particular needs and preferred treatment protocols according to physician preference, maximum tolerable daily bioavailable dosings (trough levels) for a 28-day duration is preferably about 600 micrograms of rapamycin (or equivalent) per subject kilogram for feline subjects. As another example, preferred dosing for human subjects and canine subjects is at least about one microgram per kilogram of human weight and at least about ten micrograms per kilogram of canine weight. For both human and canine subjects, a more particular preferred maximum tolerable daily bioavailable dosing (trough levels) for a multi-week duration of four weeks or less is about 200 micrograms of bioavailable rapamycin (or equivalent) per subject kilogram. Notwithstanding such examples, those of ordinary skill would understand that greater dose amount ranges may be tolerable and suitable when administered less often than once per day, and lesser ranges would be tolerable when administered more often than once per day.

In certain embodiments, it may be desirable to provide a continuous supply of a pharmaceutical composition to the patient. This could be accomplished by catheterization, followed by continuous administration of the therapeutic agent. The administration could be intra-operative or post-operative.

4. Secondary and Combination Treatments

Certain embodiments provide for the administration or application of one or more secondary or additional forms of therapies. The type of therapy is dependent upon the type of disease that is being treated or prevented. The secondary form of therapy may be administration of one or more secondary pharmacological agents that can be applied in the treatment or prevention of, for example, FCGS, gingivitis or other gingival disorder, or other autoimmune disorders or conditions associated with gingival disease or other autoimmune conditions in a patient who has been identified as being at risk for developing any of these conditions.

If the secondary or additional therapy is a pharmacological agent, it may be administered prior to, concurrently, or following administration of the inhibitor of mTOR.

The interval between administration of the inhibitor of mTOR and the secondary or additional therapy may be any interval as determined by those of ordinary skill in the art. For example, the inhibitor of mTOR and the secondary or additional therapy may be administered simultaneously, or the interval between treatments may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 hours to about 24 hours of each other and, more preferably, within about 6 hours to about 12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations. In some embodiments, the timing of administration of a secondary therapeutic agent is determined based on the response of the subject to the inhibitor of mTOR.

5. Kits

Kits are also contemplated as being used in certain aspects of the present invention. For instance, a rapamycin composition of the present invention can be included in a kit. A kit can include a container. Containers can include a bottle, a metal tube, a laminate tube, a plastic tube, a dispenser, a pressurized container, a barrier container, a package, a compartment, or other types of containers such as injection- or blow-molded plastic containers into which the hydrogels are retained. The kit can include indicia on its surface. The indicia, for example, can be a word, a phrase, an abbreviation, a picture, or a symbol.

Further, the rapamycin compositions of the present invention may also be sterile, and the kits containing such compositions can be used to preserve the sterility. The compositions may be sterilized via an aseptic manufacturing process or sterilized after packaging by methods known in the art.

General Uses of the Oral mTOR Preparations

Preferably, preparations according to the preferred embodiments are administered at a regular frequency, preferably at frequencies varying from three times per week (either on three consecutive days, or on three regularly distributed days of the week).

Although dosing may vary based on particular needs and preferred treatment protocols according to veterinarian preference, maximum tolerable daily bioavailable dosings (trough levels) for a 28-day duration are about 600 micrograms of rapamycin (or equivalent) per subject kilogram, for feline subjects. In contrast, preferred dosing for human subjects and canine subjects does not exceed preferred maximum tolerable daily bioavailable dosing (trough levels) for a multi-week duration of four weeks or less of about two hundred micrograms of bioavailable rapamycin (or equivalent) per subject kilogram, for both human and canine subjects. Nonetheless, those of ordinary skill would understand that greater dose amount ranges would be tolerable and suitable when administered less often than once per day, and lesser ranges would be tolerable when administered more often than once per day.

Whereas prior art uses of rapamycin may have involved recommended daily dosings of as low as roughly 13 micrograms per kilogram, FCGS protocols according to preferred embodiments of the present invention use higher dosings than the prior art, preferably in a range of more than 50 micrograms and up to (or even exceeding) 600 micrograms per kilogram for daily administration, or the equivalent for other frequencies of administration. Conditions addressed by oral administration protocols of the present invention include preventing and treating gingival diseases in humans, dogs and cats, whether through the preferred preparations of rapamycin (or the equivalent) or through combination therapies with stem cell therapy and/or other active pharmaceutical or botanical treatment protocols. When orally administered daily, or at other regular frequencies, in correspondingly effective doses, pharmaceutical preparations prepared according to the foregoing descriptions, and their equivalents, are effective for preventing and treating FCGS and various other maladies in humans and other animals, and for reducing the progression of those maladies and precursors, concomitants and sequelae thereof.

Specific Uses of Oral mTOR Preparations

The following disclosures describe uses of oral mTOR preparations for specific maladies, and the teachings of the present invention contemplate use of microencapsulated rapamycin nanoparticle preparations for these same purposes. In combination with background information regarding these maladies are specific example descriptions as observed by the inventors and their collaborators.

Feline Chronic Gingivo-Stomatitis (FCGS), Gingivitis & Stomatitis in General When orally administered daily, or at other regular frequencies (such as three times per week), in correspondingly effective doses, pharmaceutical preparations prepared according to the foregoing descriptions, and their equivalents, are thought to be effective for preventing and treating various autoimmune maladies in humans, canines, felines and other animals, and for delaying or reducing the progression of those maladies and their sequelae.

For example, when orally administered daily or three times per week, or at other regular frequencies, in correspondingly effective doses, pharmaceutical preparations prepared according to the foregoing descriptions, and their equivalents, are effective for preventing and treating and reducing the progression of various gingival diseases. Preferably, preparations according to the preferred embodiments are administered at a regular frequency, preferably in periods in excess of one year on a daily or three times per week regimen. Note that dosing may occur more frequently or less frequently. Particularly identified gingival diseases include gingivitis stomatitis (a/k/a gingivo-stomatitis), which includes diseases known as "lymphocytic" or "plasmacytic" gingivo-stomatitis.

For instance, positive efficacy was observed in felines with chronic gingivo-stomatitis, when microencapsulated rapamycin nanoparticle preparations according to the present invention were administered three times a week orally, in capsules containing doses at 200, 400 and 600 micrograms/kilogram, variously for two-, four-, and six-week durations. Higher dosage amounts, such as 800 micrograms/kilogram or more, and/or longer durations, such as eight weeks or more, are contemplated with some preferred microencapsulated rapamycin nanoparticle preparations for treatment of feline or other animal subjects. Particularly, in controlled studies following a protocol that confirmed the initial presence of medium to severe FCGS, an autoimmune gingival disease, microencapsulated nanoparticle preparations produced according to the process illustrated in FIGS. 2-5 not only stopped progression of FCGS in all subjects tested, but also significantly reduced the severity of FCGS in most if not all of the tested subjects. More particularly, as illustrated in FIG. 6 and discussed in more detail below in Examples 1 and 2, delineating the protocols of treating medium to severe FCGS with administration of microencapsulated nanoparticle preparations, produced according to the process illustrated in FIGS. 2-5, three times a week over 6 consecutive weeks which showed reduced severity of FCGS in all of the feline subjects that participated in the studies.

Particularly beneficial results are appreciable through regular multi-week oral administration in the prevention and treatment of FCGS as well as other gingival diseases. "Regular" oral administration may include oral administration of capsules, tablets or other oral dosing forms of microencapsulated rapamycin nanoparticles (or their equivalents) at least twice weekly, and preferably at least three times weekly, while alternative treatment protocols may be achieved through multiple dosings per day as well.

In any particular treatment protocol, it should be appreciated that dosing may vary based on particular needs and preferred treatment protocols according to preference, and depending on weight, species and other characteristics of the particular subject as well as the particular stomatitis condition for which the protocol is being applied. Those of ordinary skill would understand that greater dose amount ranges would be tolerable and suitable when administered less often than once per day, and lesser ranges would be tolerable when administered more often than once per day.

EXAMPLES

The following examples are included to demonstrate certain non-limiting aspects of the invention. It should be appreciated by those of skill in the art that the techniques disclosed in the example that follows represent techniques that are thought to function well in the practice of the invention. However, those of skill in the art, in light of the present disclosure, would also appreciate that many changes can be made in the specific embodiments that are disclosed and still obtain a like or similar result without departing from the spirit and scope of the invention.

Example 1

Figure 6A:
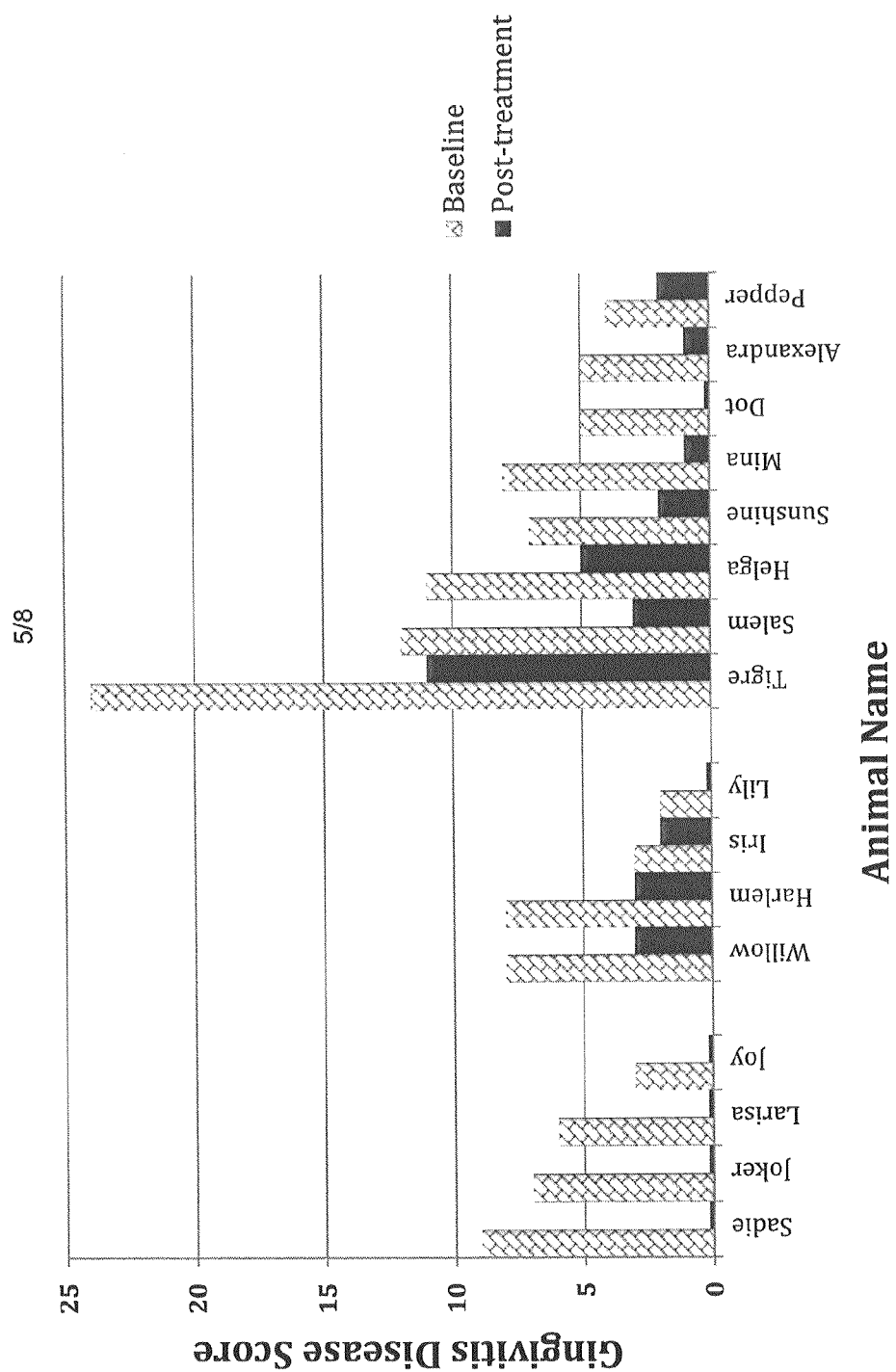
FIGS. 6A and 6B present summary data to illustrate how extended regular use of microencapsulated rapamycin nanoparticles was effective at reducing feline chronic gingivo-stomatitis (FCGS) disease scores in 100% of sixteen feline subjects.
Figure 6B:
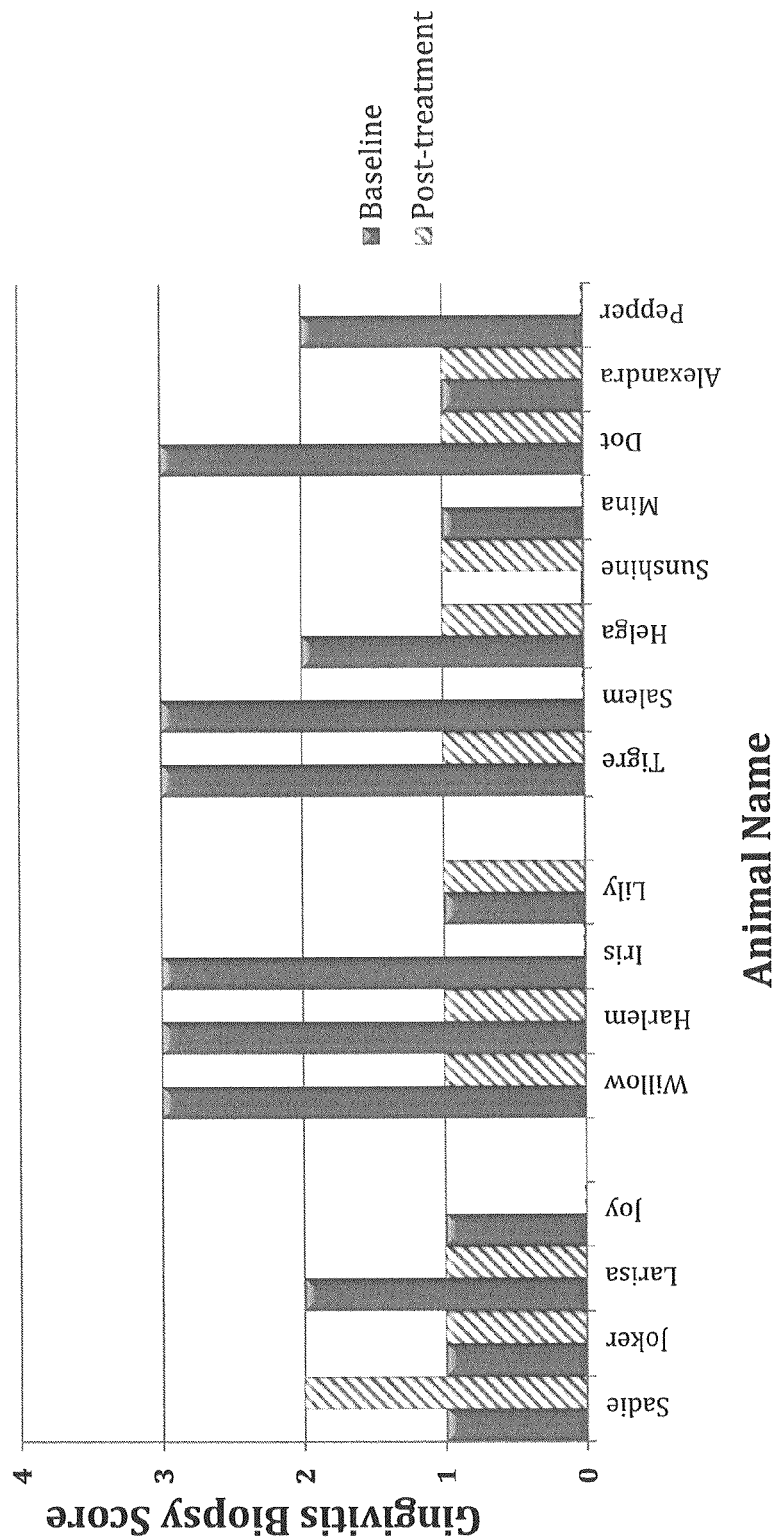

Oral administration of microencapsulated rapamycin nanoparticles has been shown to be effective in reducing the severity of FCGS, with the results of one particular study protocol illustrated in the graphs of FIGS. 6A and 6B demonstrating such a reduction in severity.

Oral administration of enteric-coated rapamycin nanoparticles in capsule form occurred over a 6-week period in order to evaluate the efficacy of the orally administered rapamycin in the treatment of feline gum disease. Animals were chosen based on oral examination revealing moderate persistent gingival inflammation and/or oral pathology representative of feline gingivo-stomatitis. Four days prior to the first administration of rapamycin, the study animals were examined and the affected tissues were assigned a score based, in part, on the severity of the condition according to pre-established study protocol, with these initial scores being plotted as the Baseline in FIG. 6A. In assigning each study subject a score for baseline purposes, eight regions of the oral cavity were evaluated on examination and assigned a score on a 4-point scale based on severity of disease observed for each region. Specifically, the scale was characterized as follows: 0—No inflammation; 1—Mild inflammation, slight redness in color, slight edema, no bleeding on probing; 2—Moderate inflammation, moderate glazing, redness, bleeding on probing. Mild proliferation or ulceration of the gums may be present; and 3—Severe inflammation, marked redness and hypertrophy, ulceration, tendency to spontaneous bleeding, marked proliferation/ulceration of the gums. The eight regions of the oral cavity to which scores were assigned were: upper canines and incisors; lower canines and incisors; upper right premolars and molars; upper left premolars and molars; lower right premolars and molars; lower left premolars and molars; right palatoglossal folds and fauces; and left palatoglossal folds and fauces. Therefore, the maximum total score for any study subject was 24 (8 (regions)×3 (maximum score per region)). Overall, the mean baseline score across the study group was 7.6 out of a possible 24.

Biopsies of affected tissue were taken by punch biopsy or excision prior to enteric-coated rapamycin nanoparticle administration at the initial oral examination and again following the oral examination at the termination of treatment, with the tissues being submitted for histopathology analysis. The site of the biopsy was selected from the region of greatest inflammation in which a minimum of 3 mm biopsy punch could be collected. The final biopsy was taken from the region adjacent to the original biopsy site. Each study subject was assigned a baseline biopsy score rated on a 4-point scale corresponding to none, mild, moderate, or severe inflammation. These baseline biopsy scores are illustrated in the graph in FIG. 6B, which also plots the post-treatment biopsy scores for each of the study subjects.

Feline subjects were given between about 400 and 600 µg/kg of enteric-coated rapamycin nanoparticles, a preferred form of enteric-coated nanoRapa. Within that range, specific desired dosages were resolved and determined based in part on the weight of each subject. Feline subjects initially received enteric-coated rapamycin nanoparticles three times per week over a two-week period. More particularly, for each treated subject, the same quantity of the same rapamycin preparation was administered on Days 1, 3, 5, 8, 10, and 12 during the first two-week regimen (Cycle 1). After assessing results of the first two-week regimen, a desired quantity of the same rapamycin preparation was administered on Days 15, 17, 19, 22, 24, and 26 in a second 2-week regimen (Cycle 2) of the study, which immediately followed the first two-week regimen. For assessing results after the first two-week regimen, each subject animal had its oral cavity examined on day 13, following the end of Cycle 1. For assessing results after the second two-week regimen, each subject animal had its oral cavity examined on Day 27, following the end of Cycle 2.

Results of those treatments are illustrated as the "Post-Treatment Scores" for each study subject in FIG. 6A, these results indicating that, in every instance, the severity of gingival disease was reduced. Overall, the mean post-treatment score across the study group was 2.1 out of 24, down from a mean of 7.6 prior to administration of the first enteric-coated rapamycin nanoparticle regimen. In all but one of the treated animals, the reduction of the severity of the disease was more than 50%. In 43.8% of the animals treated, the disease was nearly eliminated altogether.

Differences in biopsy scores also indicate that the preferred enteric-coated rapamycin nanoparticle preparation is effective in treating FCGS. As illustrated in FIG. 6B, the biopsy score dropped for eleven out of the sixteen animals following treatment with enteric-coated rapamycin nanoparticles. Overall, the mean biopsy score for the study group dropped from 1.875 prior to drug administration to a mean of 0.75 after drug administration was completed. Thus, orally administered enteric-coated rapamycin or enteric-coated rapamycin nanoparticles, at a dosage of 400-600 µg/kg, has shown to be effective in treating chronic gingivo-stomatitis in cats.

Example 2

Figure 7A:
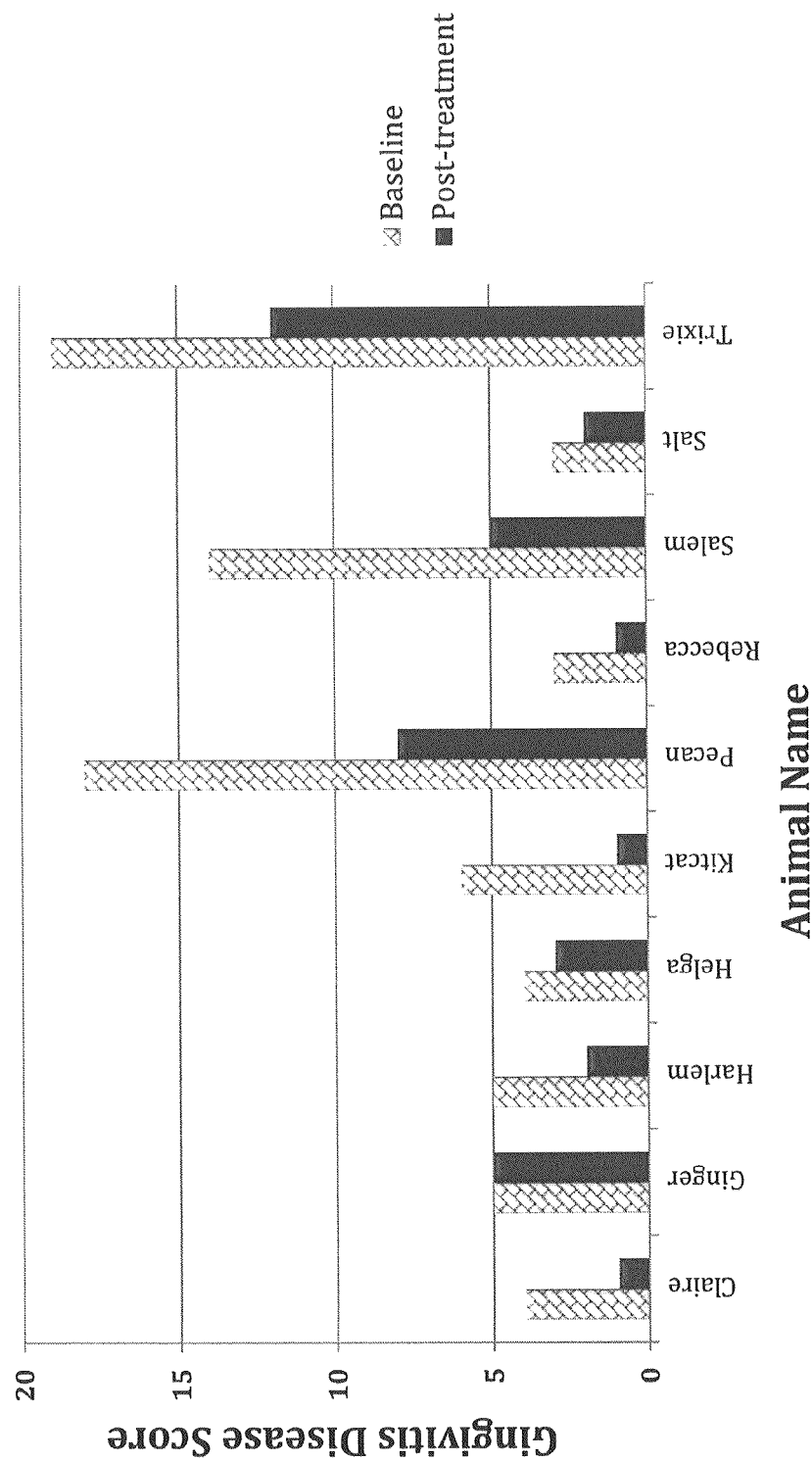
FIGS. 7A and 7B present summary data to illustrate how extended regular use of microencapsulated rapamycin nanoparticles administered was effective at reducing FCGS disease scores in 90% of ten feline subjects, even at a lower dose than what was administered in a previous study, the results of the previous study being represented in FIGS. 6A and 6B.
Figure 7B:
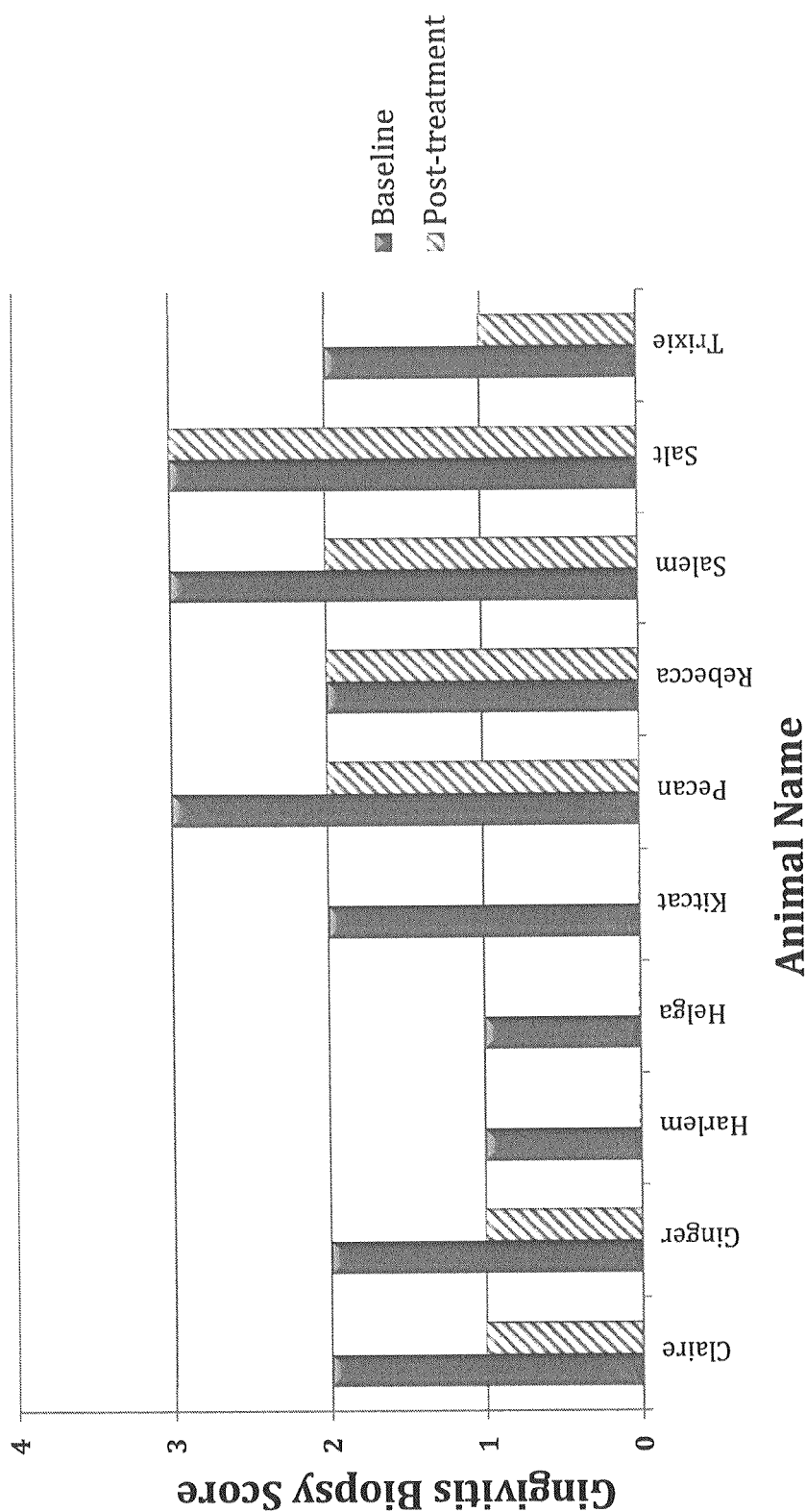

The goal of this particular study was to evaluate the effectiveness of rapamycin (particularly, enteric-coated rapamycin nanoparticles) in treating chronic, persistent or refractory inflammatory diseases of the gums and oral cavity that are not responsive to dentistry and antibiotic therapy. Specifically, the present study examined the effectiveness of a lower dose of enteric-coated rapamycin nanoparticles, specifically 200 µg/kg of body weight for each study subject. The results of this study are illustrated in FIGS. 7A and 7B.

Thirteen domestic cats were selected to enter the trial based on inflammatory appearance of the gums discovered during veterinary examinations performed prior to initiation of the study. An additional criterion for selection was that of good general health (other than gingival inflammation) as determined by baseline veterinary physical examinations, urinalysis, and complete blood count and biochemistry analysis. The cats selected were of both sexes and ranged from 3 to 13 years of age. Baseline blood for a complete blood count (CBC) and superchemistry parameters and urine for urinalysis was collected from animals on Day-22. A full oral examination was carried out to determine the level of inflammatory gum disease. Following the oral examination, each study subject received a dental cleaning and 7 days of antibiotic therapy, with each animal receiving either a 62.5 mg dose or a 125 mg dose of Aventiclav (amoxicillin/clavulanic acid) twice daily, the dosage being based on the weight of the animal.

On Day-4, oral examination was repeated to determine the presence of any disease and each animal was then assigned a baseline score based on the severity of disease observed. Eight regions of the oral cavity (upper canines and incisors; lower canines and incisors; upper right premolars and molars; upper left premolars and molars; lower right premolars and molars; lower left premolars and molars; right palatoglossal folds and fauces; and left palatoglossal folds and fauces) were scored for each study subject on a 4-point scale. The scale was characterized as follows: 0—No inflammation; 1—Mild inflammation, slight redness in color, slight edema, no bleeding on probing; 2—Moderate inflammation, moderate glazing, redness, bleeding on probing. Mild proliferation or ulceration of the gums may be present; 3—Severe inflammation, marked redness and hypertrophy, ulceration, tendency to spontaneous bleeding, marked proliferation/ulceration of the gums. Since each of the eight regions was scored for each study subject, the maximum possible score for an individual subject was 24 (3×8). Blood and urine were also collected which provided additional baseline data. Three animals scored lower than 3 at the time of the initial assessment, displaying a positive response to the previously administered dental work and antibiotic therapy. These animals were not entered into the treatment phase of the trial. The animals that exhibited disease present on oral examination following the dentistry and antibiotic therapy were selected for the treatment phase of the trial.

Biopsies were taken by punch biopsy or excision from the affected tissue and submitted for histopathology analysis after the initial oral examination. Baseline biopsies of gum tissue were collected, such biopsies being taken from the area of the gums which had the highest level of inflammation, and scores were assigned for each specimen based on a 4-point scale (0-3) corresponding to the level of inflammation observed, the levels being no inflammation, mild inflammation, moderate inflammation, or severe inflammation. The final biopsy, performed following the full enteric-coated rapamycin nanoparticle treatment regimen, was taken from a region adjacent to the original biopsy site. Baseline biopsy scores for each study subject, as well as post-treatment biopsy scores, are illustrated in FIG. 6B.

Prior to beginning the enteric-coated rapamycin nanoparticle treatment regimen, the study subjects were given a three-day rest period to heal following the baseline assessment. Baseline Quantitative Magnetic Resonance (QMR) analysis was performed on all animals within this time period. The animals then entered two 2-week dosing cycles with enteric-coated rapamycin nanoparticles. During the first 2-week drug administration cycle, enteric-coated rapamycin nanoparticle preparations were administered orally on Saturday, Monday and Wednesday (i.e. the drug was given every other day for 5 days). There was then a 2-day break, which was followed by another every-other-day treatment regime. One day after the last administered dose of the first 2-week dosing cycle, subjects underwent veterinary exams during which blood and urine were collected and their gum tissues examined and scored. At the end of the first dosing cycle, 8 out of 10 cases showed improvement based on the newly assigned gum tissue scores. In the other two cases, there was no change. The second 2-week drug administration cycle resumed with the same dosing regimen described above (i.e. treatment with enteric-coated rapamycin nanoparticles every other day) with the same examination routine of each study subject occurring one day after the last administered dose in the cycle. There was little further improvement at the end of the second 2-week dosing cycle, with some animals showing partial reversion.

A third 2-week dosing cycle was added to the trial. At the completion of the third dosing cycle, final physical and oral examinations were performed, and blood and urine were collected. In addition, biopsies were taken for subsequent histological analysis by the University of Guelph Animal Health Laboratory. As illustrated by the graph in FIG. 6A, when compared to baseline, 9 out of 10 subjects showed improvement which was statistically significant (p=0.005). A second biopsy was also collected for submission to the bioanalytical laboratory for measurement of drug concentration within the gum tissue. According to the biopsy data, eight out of ten animals showed improvement and two animals were unchanged. Using the Wilcoxon Matched Pairs Test, the difference was found to be highly significant (t=2.5205; p=0.01117). The biopsy results are shown in FIG. 6B. After completing the gum biopsies, QMR scans were performed on the last day of the study and compared with QMR results at baseline. There were no statistically significant changes, although there was a marginally significant increase in the ratio of fat to body weight (p=0.06).

Alternative Embodiments with Other Rapamycins

Although many aspects of the present invention relate directly to rapamycin itself, possible broader aspects of the invention relate also to analogs and derivatives of rapamycin, and to producing a more stable and effective oral preparation for delivering an agent to bind, interact with or otherwise regulate activity of the mTOR pathway.

Accordingly, as alternatives that benefit from many but not necessarily all of the teachings of the present invention, any of the particular embodiments described above may be modified by substituting one or more other rapamycins in place of (or in addition to) rapamycin. For corresponding purposes of these descriptions, rapalogs and all mTOR pathway inhibitors should be considered as "rapamycins" (i.e., the plural of rapamycin). Also, in this context and wherever else a context relates to any of the rapamycins rather than just rapamycin, any related references to "encapsulated rapamycin" should be read as teaching not only about discrete particles that include rapamycin, but also about discrete particles that include any one or more rapamycins. It should also be understood that reference to any "encapsulated" form (including "microencapsulated" forms) should be interpreted to disclose a form that in some embodiments is fully encapsulated; provided however, that reference to an "encapsulated" form does not necessarily mean that all embodiments of that form are completely encapsulated; rather, it should be understood that reference to an "encapsulated" form, without more, encompasses a form that may only be partially encapsulated, except to the extent clarified or reasonably understood otherwise.

Administration in Combination with Other Therapies

It should also be understood that the foregoing disclosure emphasizes certain specific embodiments of the invention. Alternative embodiments may involve administration of rapamycin in combination with other therapies. Such therapies include but are not limited to dental scaling; long term use of antibacterial dental hygiene products; professional scaling and long-term tooth brushing with 0.2% chlorohexidine; corticosteroids; gold salts; antibiotics; chlorohexidine gluconate gel; radical dental extraction techniques of premolars, molars or other teeth; radiation therapy; cryotherapy; antibiotics with activity against gram-negative and anaerobic organisms (including amoxicillin-clavulanic acid combination, enrofloxacin, lincomycin, clindamycin, spiramycin, metronidazole, and tetracyclines); subgingival injection of up 10 milligrams triamcinolone; long-term prednisolone, methylprednisolone, or triamcinolone; methylpredinisolone; sodium aurothiomalate; aurothioglucose; azathioprine; cyclophosphamide; chlorambucil; immunostimulatory; PIND-ORF; megoestrol acetate; lactoferrin; sodium salicylate; meloxicam; interferon; thalidomide; anti-viral agents; azidothymidine (AZT); PMEA; soft-tissue lasers; multivitamin; antioxidant supplementation; and chemical cautery.

General Alternatives

Various embodiments have been described in terms of methods and preparations for treating FCGS and other specific maladies or conditions. It should be recognized, though, that alternative embodiments are not limited to methods or preparations for treating those maladies or conditions as such, but are instead methods for treating, preventing or managing other conditions that are related in one way or another to the maladies or conditions that are specifically mentioned. For these purposes, conditions related to FCGS or other maladies or conditions identified herein generally include conditions that are precursors, concomitants and sequeale of those maladies and conditions that are actually named. For these purposes, related conditions also include analogous maladies or conditions that are known to occur in different species than the species for which a particular embodiment is described. For instance, as one example with respect to FCGS, any stomatitis in feline subjects would, without more, be presumed to be a related condition for these purposes, as would any stomatitis in humans or other non-feline animal subjects.

Some of the teachings of the present invention described in terms of a method of treating a condition are also alternatively embodied as methods of administering the described preparations, for useful ends relative to the types of subjects mentioned herein, as well as methods for reliably producing and administering chemical preparations. Related embodiments also represent pharmaceutical preparations that would be suitable for such uses, as well as methods for making such pharmaceutical preparations.

It should be understood that the foregoing disclosure emphasizes certain specific embodiments of the invention and that all substitutions, modifications or alternatives equivalent thereto should be presumed to fall within the spirit and scope of the invention. While reference is made in many respects to incorporation of various rapamycin nanoparticle embodiments, it should also be recognized that the spirit and scope of the invention may not be limited to nanoparticles as such, nor to the other particular compounds or the like referenced herein.

In all respects, it should also be understood that the drawings and detailed description herein are to be regarded in an illustrative rather than a restrictive manner, and are not intended to limit the invention to the particular forms and examples disclosed. Rather, the invention includes all embodiments and methods within the scope and spirit of the invention as claimed, as the claims may be amended, replaced or otherwise modified during the course of related prosecution. Any current, amended, or added claims should be interpreted to embrace all further modifications, changes, rearrangements, substitutions, alternatives, design choices, and embodiments that may be evident to those of skill in the art, whether now known or later discovered. In any case, all substantially equivalent systems, articles, and methods should be considered within the scope of the invention and, absent express indication otherwise, all structural or functional equivalents are anticipated to remain within the spirit and scope of the present inventive system and method.

It is also specifically contemplated that any of the particular encapsulated rapamycin embodiments described herein may be provided in daily oral doses (once or twice daily) for any of the medical or veterinary applications referenced throughout this specification or that may be referenced in US Patent Application 2012/0064143 and any other publications describing possible uses for encapsulated rapamycin. It should also be understood that the dosing regimens described herein with regard to specific indications may also be used with any or all of the other indications discussed. Dosing regimen would include both the concentration of rapamycin administered as well as the frequency of administration.

Alternative embodiments of the present invention include administering rapamycin locally to the oral cavity and at least one polymer, such that said system is attached to a surface in the oral cavity and remains attached thereto for at least 1 hour. Administration may also include a sustained release and a liquid precursor varnish composition to this system. This process is discussed in detail in Friedman et al., (US 2013/0018069), which is incorporated by reference.

For other alternatives, it should be understood that any limitation discussed with respect to one embodiment of the invention may apply to any other embodiment of the invention. Moreover, any composition of the invention may be used in any method of the invention, and any method of the invention may be used to produce or to utilize any composition of the invention. Any embodiment of the present invention may consist of or consist essentially of—rather than comprise/include/contain/have—the described features and/or steps.

Accordingly and otherwise, many other alternatives will be evident to those of skill in the art. Rather than being limited by the embodiment descriptions as set forth above, the invention itself should ultimately be contemplated based on any claims that may be appended hereto or added in the course of prosecuting this patent application or other patent applications that claim direct or indirect priority to this patent application. All descriptive materials referenced herein are incorporated by reference in their entirety, for all purposes.

With the understanding that any recited examples and alternatives introduced by "such as," "for example" or the like are included as non-living examples of an antecedent in order to enhance comprehension through readability, we claim the following inventions:

1. A method for treating feline chronic gingivo-stomatitis (FCGS) through oral administration of a pharmaceutical preparation, comprising:
   a. preparing or otherwise obtaining a microparticle pharmaceutical preparation, comprising:
      i. a solid excipient matrix comprising a polymer composition that generally retains its structure when exposed to acidic conditions of the alimentary canal of a typical domestic feline subject and that disintegrates in neutral to basic conditions of intestinal portions of the alimentary canal of a typical domestic feline subject; and
      ii. mTOR inhibiting nanoparticles dispersed within said solid excipient matrix, said mTOR inhibiting nanoparticles comprising microscopic structures and pharmaceutically active cores within said microscopic structures;
      iii. said pharmaceutically active cores comprising a pharmaceutically active mTOR inhibiting compound;
      iv. said microscopic structures comprising an aqueous-soluble, amphoteric compound;

v. said amphoteric aqueous-soluble compound comprising sodium cholate;
b. orally administering said microparticle pharmaceutical preparation to a feline subject having FCGS; and
c. repeating oral administration of said microparticle pharmaceutical preparation to said feline subject multiple times per week over a multi-week duration, in amounts such that said feline subject is administered said pharmaceutically active compound in amounts and over durations that are efficacious for reducing the severity of FCGS in said feline subject.

2. The method of claim 1, wherein said orally administering step comprises orally administering said preparation at a frequency of three or more times per week, in a dosage that is therapeutically effective for preventing or treating said autoimmune maladies in the animal subject when administered at said frequency.

3. The method of claim 1, wherein said repeating oral administration step comprises administering said microparticle pharmaceutical preparation in amounts such that said feline subject is administered said compound in amounts, and frequencies and over durations that are efficacious for treating as one or more of the following: gingival disease; Feline Chronic Gingivo-Stomatitis; autoimmune mucous membrane oropharyngeal maladies; and precursors, concomitants and sequelae of any of the foregoing.

4. The method of claim 1, wherein said pharmaceutical preparation is administered to said animal subject wherein said animal subject is in need of prevention or treatment, or delayed progression, of Feline Chronic Gingivo-Stomatitis (FCGS).

5. The method of claim 4, wherein a dosage of said pharmaceutical preparation provides between one microgram/kilogram and 800 micrograms/kilogram weight of said feline subject.

6. The method of claim 5, wherein said dosage is administered at least three times per week for a duration of two, four, six or eight weeks.

7. The method of claim 1, wherein said microscopic structures comprise micelles.

8. The method of claim 1, wherein said amphoteric, aqueous-soluble compound has properties that tend to naturally induce the formation of micelles within an aqueous solution of said amphoteric, aqueous-soluble compound.

9. The method of claim 7 wherein said microscopic structures have properties that promote stability of said mTOR inhibitor when said mTOR inhibiting nanoparticles are dispersed with said matrix.

10. The method of claim 1, further comprising:
a. producing a dispersion of rapamycin nanoparticles, said production step comprising:
   i. dissolving said rapamycin in a water-miscible solvent to form a rapamycin solution;
   ii. dissolving a water-soluble surfactant in a quantity of deionized water to form a surfactant solution, wherein said surfactant is at a concentration above its critical micelle concentration;
   iii. transferring a measure amount of said surfactant solution to a container and stirring said surfactant solution; and
   iv. adding a measured amount of said rapamycin solution to said surfactant solution, as well as a measured amount of glycerol, while said surfactant is being stirred.

11. The method of claim 10, wherein said rapamycin solution and said surfactant solution are combined and mixed in a continuous flow apparatus.

12. The method of claim 10, wherein the volumetric ratio of the rapamycin solution to the surfactant solution is between about 1:10 to 1:1.

13. The method of claim 10, wherein the volumetric ratio of the rapamycin solution to the surfactant solution is between about 1:5 to 1:1.

14. The method of claim 10, wherein said rapamycin is dissolved in said water-miscible solvent at a concentration of between about 0.01% weight to volume to about 15% weight to volume.

15. The method of claim 10, wherein said rapamycin is dissolved in said water-miscible solvent at a concentration of between about 1% weight to volume to about 15% weight to volume.

16. A method for treating feline chronic gingivo-stomatitis (FCGS) through oral administration of a pharmaceutical preparation, comprising:
a. obtaining a pharmaceutical preparation, comprising
   i. a solid excipient matrix comprising a methacrylic acid and methyl methacrylate copolymer composition; and
   ii. rapamycin nanoparticles dispersed within said solid excipient matrix;
   iii. each of said rapamycin nanoparticles comprising a sodium cholate and a pharmaceutically active core comprising rapamycin; and
b. orally administering said pharmaceutical preparation to a feline subject having FCGS; and
c. repeating oral administration of said pharmaceutical preparation to said feline subject multiple times per week over a multi-week duration, in amounts efficacious for reducing the severity of FCGS in said feline subject.

17. The method of claim 16, wherein said solid excipient matrix has a pH of about 8 or less.

18. The method of claim 16, wherein said copolymer composition is essentially insoluble at a pH less than 7, and wherein said copolymer composition dissolves at a pH greater than about 7.

19. The method of claim 18, wherein said copolymer comprises methacrylic acid and methyl methacrylate at a comonomer ratio of 1:2, respectively.

20. The method of claim 18, wherein said copolymer comprises methacrylic acid and methyl methacrylate at a comonomer ratio of 1:1.

21. The method of claim 16, wherein said rapamycin nanoparticles are sized in the range between about 1 nanometer and about 1 micron.

* * * * *

UNITED STATES PATENT AND TRADEMARK OFFICE
CERTIFICATE OF CORRECTION

PATENT NO. : 9,283,211 B1
APPLICATION NO. : 14/717844
DATED : March 15, 2016
INVENTOR(S) : Dana M. Vaughn Page 1 of 1

It is certified that error appears in the above-identified patent and that said Letters Patent is hereby corrected as shown below:

On the Title Page

In the "Related U.S. Application Data" section:
After Item "(63) Continuation of application No. PCT/US2015/026266, filed on Apr. 16, 2015."
Insert: -- (60) Provisional application No. 61/980,095, filed on April 16, 2014 --

Signed and Sealed this
Second Day of June, 2020

Andrei Iancu
*Director of the United States Patent and Trademark Office*